United States Patent
Acosta et al.

(10) Patent No.: US 9,435,791 B2
(45) Date of Patent: Sep. 6, 2016

(54) METHOD FOR USING NANODIAMONDS TO DETECT NEARBY MAGNETIC NANOPARTICLES

(71) Applicant: Verily Life Sciences LLC, Mountain View, CA (US)

(72) Inventors: Victor Marcel Acosta, San Francisco, CA (US); Vikram Singh Bajaj, Mountain View, CA (US); Jason Donald Thompson, Palo Alto, CA (US); Eric Peeters, San Jose, CA (US)

(73) Assignee: Verily Life Sciences, LLC, Mountain View, CA (US)

( * ) Notice: Subject to any disclaimer, the term of this patent is extended or adjusted under 35 U.S.C. 154(b) by 0 days.

(21) Appl. No.: 14/318,220

(22) Filed: Jun. 27, 2014

(65) Prior Publication Data

US 2015/0377865 A1 Dec. 31, 2015

(51) Int. Cl.
*A61K 49/00* (2006.01)
*G01N 33/50* (2006.01)
*A61B 5/1455* (2006.01)
*G01N 33/543* (2006.01)
*G01N 33/544* (2006.01)

(52) U.S. Cl.
CPC ......... *G01N 33/5091* (2013.01); *A61B 5/1455* (2013.01); *G01N 33/544* (2013.01); *G01N 33/54333* (2013.01); *G01N 33/54346* (2013.01); *A61K 49/001* (2013.01); *A61K 49/0002* (2013.01)

(58) Field of Classification Search
None
See application file for complete search history.

(56) References Cited

U.S. PATENT DOCUMENTS

| 8,193,808 B2 | 6/2012 | Fu et al. |
| 8,617,824 B2 | 12/2013 | Poetter et al. |
| 2008/0226562 A1* | 9/2008 | Groves .............. A61K 49/0002 424/9.6 |

(Continued)

FOREIGN PATENT DOCUMENTS

| WO | 2010051580 A1 | 5/2010 |
| WO | 2013/066446 A1 | 5/2013 |

(Continued)

OTHER PUBLICATIONS

International Search Report and Written Opinion of International Application No. PCT/US2015/034247 dated Aug. 28, 2015 (mailed Aug. 28, 2015).

(Continued)

*Primary Examiner* — Rebecca Martinez
(74) *Attorney, Agent, or Firm* — McDonnell Boehnen Hulbert & Berghoff LLP

(57) ABSTRACT

An imaging agent for detecting analytes in an environment includes functionalized nanodiamonds and functionalized magnetic particles that can selectively interact with an analyte. Each functionalized nanodiamond contains at least one color center configured emit light in response to illumination. At least one property of the light emitted by the color centers is related to the proximity of the functionalized magnetic particles to the color centers. This property can be detected to determine that the functionalized nanodiamonds are proximate to the functionalized magnetic particles, to determine that the functionalized nanodiamonds and the functionalized magnetic particles are interacting with the analyte, or other applications. Devices and methods for detecting properties of the analyte by interacting with the functionalized nanodiamonds and functionalized magnetic particles are also provided.

20 Claims, 18 Drawing Sheets

(56) References Cited

U.S. PATENT DOCUMENTS

| | | | |
|---|---|---|---|
| 2010/0188075 A1* | 7/2010 | Litvinov | G01N 33/54373 324/214 |
| 2010/0324389 A1 | 12/2010 | Moon et al. | |
| 2011/0006218 A1* | 1/2011 | Mochalin | B82Y 30/00 250/459.1 |
| 2011/0062957 A1 | 3/2011 | Fu et al. | |
| 2012/0019242 A1 | 1/2012 | Hollenberg et al. | |

FOREIGN PATENT DOCUMENTS

| | | | |
|---|---|---|---|
| WO | 2013066446 A1 | 5/2013 | |
| WO | 2013188651 A1 | 12/2013 | |
| WO | 2014/014970 A1 | 1/2014 | |

OTHER PUBLICATIONS

Acosta, Victor and Hemmer, Philip, Nitrogen-vacancy centers: Physics and applications, Materials Research Society Bulletin, vol. 38, pp. 127-130 (Feb. 2013).

Acosta, VM et al., High nitrogen-vacancy density diamonds for magnetometry applications, Physical Review B, 80, 115202 (2009).

Acosta, VM et al., Temperature dependence of the nitrogen-vacancy magnetic resonance in diamond, Physical Review Letters, 104, 70801 (2010).

Toyli, DM, et al., Measurement and control of single nitrogen-vacancy center spins above 600K, Phys. Rev. X 2, 31001 (2012).

Shin, Chang S et al., Room-temperature operation of a radiofrequency diamond magnetometer near the shot-noise limit, Journal of Applied Physics, 112, 124519 (2012).

Taylor, JM et al., High-sensitivity diamond magnetometer with nanoscale resolution, Nature Physics, vol. 4, pp. 810-816 (2008).

Jarmola, A et al., Temperature and magnetic field dependent longitudinal spin relaxation in nitrogen-vacancy ensembles in diamond, Physical Review Letters, 108, 197601 (2012).

Loretz, M et al., Radio-frequency magnetometry using a single electron spin, Physical Review Letters, 110, 017602 (2013).

Staudacher, T et al., Nuclear magnetic resonance spectroscopy on a (5-nanometer)3 sample volume, Science, vol. 339, pp. 561-563 (Feb. 2013).

Zhang, Yi and Zhai, Ya, Magnetic induction heating of nano-sized ferrite particle, Advances in Induction and Microwave Heating of Mineral and Organic Minerals, Ch. 21 (Feb. 2011).

Kucsko, G et al., Nanometre-scale thermometry in a living cell, Nature, vol. 500, pp. 54-59 (Aug. 2013).

* cited by examiner

METHOD FOR USING NANODIAMONDS TO DETECT NEARBY MAGNETIC NANOPARTICLES

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body was of scientific interest. The one or more analytes could be cofactors, substrates, products, or other substances related to a drug under development. The one or more analytes could be present in living or nonliving human or animal tissue, and could be detected and/or measured in an in vivo, ex vivo, in vitro, or some other type of sample. The one or more analytes could include enzymes, reagents, hormones, proteins, cells or other molecules.

SUMMARY

Some embodiments of the present disclosure provide a method including: (i) exposing an environment to illumination, wherein the environment includes functionalized nanodiamonds and functionalized magnetic nanoparticles, wherein each of the functionalized nanodiamonds contains at least one color center and is functionalized to selectively interact with an analyte in the environment, wherein each of the magnetic nanoparticles is functionalized to selectively interact with the analyte in the environment, and wherein the illumination causes individual color centers to emit light having one or more properties relating to proximity between the individual color centers and the functionalized magnetic nanoparticles; and (ii) detecting the one or more properties of the light emitted by the color centers in response to the illumination.

Some embodiments of the present disclosure provide an imaging agent including: (i) a plurality of functionalized magnetic nanoparticles, wherein each of the magnetic nanoparticles is functionalized to selectively interact with an analyte in an environment; and (ii) a plurality of functionalized nanodiamonds, wherein each of the functionalized nanodiamonds contains at least one color center and is functionalized to selectively interact with the analyte in the environment, and wherein the at least one color center is configured to emit light in response to illumination, wherein the emitted light has one or more properties relating to proximity between the at least one color center and individual functionalized magnetic nanoparticles of the plurality of functionalized magnetic nanoparticles.

Some embodiments of the present disclosure provide a device including: (i) a light source configured to expose an environment to illumination, wherein the environment includes functionalized nanodiamonds and functionalized magnetic nanoparticles, wherein each of the functionalized nanodiamonds contains at least one color center and is functionalized to selectively interact with an analyte in the environment, wherein each of the magnetic nanoparticles is functionalized to selectively interact with the analyte in the environment, and wherein the illumination causes individual color centers to emit light having one or more properties relating to proximity between the individual color centers and the functionalized magnetic nanoparticles; and (ii) a light sensor configured to detect one or more properties of light emitted by the color centers in response to the illumination.

These as well as other aspects, advantages, and alternatives, will become apparent to those of ordinary skill in the art by reading the following detailed description, with reference where appropriate to the accompanying drawings.

DETAILED DESCRIPTION

Figure 1A:
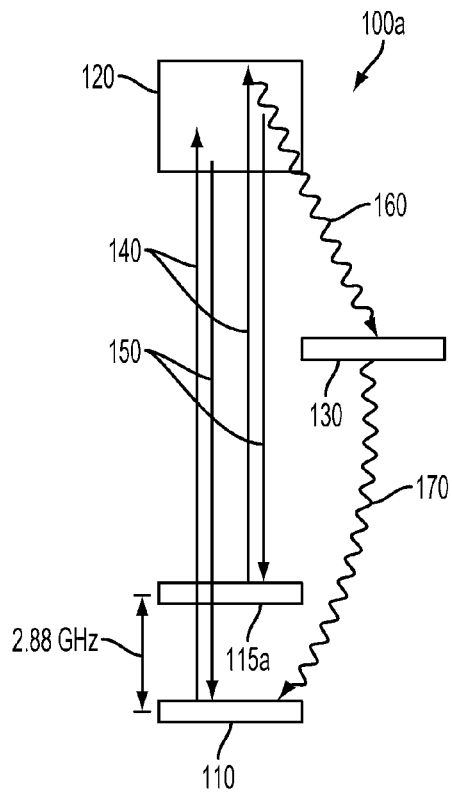
FIG. 1A is an energy diagram of an example color center.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a gel, an emulsion, a fluid conduit, a fluid reservoir, etc. For example, one of skill in the art will recognize that the embodiments disclosed herein may be used to sense analytes present in a water treatment system. Moreover, while the present disclosure describes embodiments for use in vivo, one of skill in the art will also recognize that in vitro applications are possible as well. Accordingly, the environment may also include a test tube or other vessel for holding a fluid.

I. Overview

An imaging agent including functionalized, color-center doped nanodiamonds and functionalized magnetic nanoparticles could be used to determine the presence, concentration, and/or other properties of one or more analytes in an environment (e.g., a biological environment within a human body). Individual color centers (for example, negatively-charged nitrogen vacancy centers, sometimes referred to as nitrogen vacancy color centers, nitrogen vacancy defects, or nitrogen color centers) in diamond can be illuminated (e.g., from about 500 nanometers to about 650 nanometers for negatively-charged nitrogen vacancy centers) and can emit light in response to the illumination (e.g., from about 650 nanometers to 800 nanometers for negatively-charged nitrogen vacancy centers). Functionalized magnetic nanoparticles can include ferromagnetic, paramagnetic, or other magnetically active elements (e.g., a particle of superparamagnetic iron oxide (SPIO)). One or more properties of light emitted in response to illumination by individual color centers in the functionalized nanodiamonds could be related to a magnetic field produced and/or affected by functionalized magnetic nanoparticles proximate to the functionalized nanodiamonds. The nanodiamonds and the magnetic nanoparticles could be functionalized with the same or different receptors, proteins, antibodies, DNA sequences, and/or other materials such that the nanodiamonds and magnetic nanoparticles selectively interact with the one or more analytes, allowing the presence of the one or more analytes to be inferred by the detection of functionalized nanodiamonds located proximate to functionalized magnetic nanoparticles.

The imaging agent could be introduced into an environment. Light could be emitted into the environment such that color centers in the nanodiamonds of the imaging agent emit light. The color centers could include negatively-charged nitrogen vacancy centers. Additionally or alternatively, the color centers could include other crystal defects exhibiting optical properties that are related to the magnetic field in the environment of the color centers. For example, the color centers could have more than one spin state, illumination of the color centers could affect the occupancy of the spin states, emission of light in response to illumination could be related to the occupancy of the spin states, and magnetic fields could affect the occupancy of the spin states. One or more properties of the emitted light (e.g., amplitude, location time between light pulses) could be detected and used to determine one or more properties of the imaging agent in the environment (e.g., the location of individual functionalized nanodiamonds, the presence of functionalized magnetic nanoparticles proximate to individual functionalized nanodiamonds, the direction magnitude, spectrum, or other properties of the magnetic field in the environment of the nanodiamonds). The determined one or more properties of the emitted light in the environment could be used to determine the presence, location, concentration, and/or other properties of the one or more analytes in the environment. For example, the environment could be a human body and the one or more analytes could be cancer cells. The elements of the imaging agent (i.e., nanodiamonds, magnetic nanoparticles) could be functionalized to selectively bind to the cancer cells and/or to elements of the cancer cells. The presence of the cancer cells in the human body could be detected by detecting one or more properties of the light emitted by the nanodiamonds in the human body and determining, based on the detected one or more properties, that the nanodiamonds were proximate to the magnetic nanoparticles.

In some examples, the illumination could be pulsed, and the timing, duration, amplitude, and other properties of the pulses could be specified to enable detection of the magnetic field in the environment of the color centers, and this detection could be used to infer the presence of functionalized magnetic nanoparticles proximate to the functionalized nanodiamonds. For example, a first pulse at a first point in time could effect a change in the occupancy of spin states in the color centers of the nanodiamonds, and a second pulse at a second time could cause the emission of light by the color centers. One or more properties of the emitted light at the second point in time could be related to the occupancy of the spin states at the second point in time. A change in the occupancy of the spin states over time could be determined based on one or more detected properties of the emitted light at the second point in time (e.g., the amplitude of the emitted light), and one or more properties of the magnetic field in the environment of the color centers could be determined based on the determined change in the occupancy of the spin states over time.

Electromagnetic radiation and/or a static or alternating magnetic field could additionally be applied to the environment to control and/or alter the properties of the functionalized nanodiamonds and/or functionalized magnetic nanoparticles. The applied electromagnetic energy could affect one or more properties of the color centers in the nanodiamond and/or of the light emitted by the color centers. In some examples, the electromagnetic radiation could include microwave radiation having a specified frequency, or have a sequence of frequencies over time, to enable optical detection of magnetic resonance (ODMR) of color centers in the functionalized nanodiamonds. For example, the degree of fluorescence of the color centers could be detected at a plurality of points in time when the color centers were exposed to a respective plurality of frequencies of microwave radiation, allowing an ODMR spectrum to be wholly or partially determined.

Features of the ODMR spectrum could be used to determine one or more properties of the color centers and/or of the environment of the color centers. Some color centers (e.g., negatively-charged nitrogen vacancies) could exhibit a resonance peak spreading due to a static or quasi-static magnetic field; e.g., a magnetic field produced by a magnetic nanoparticle proximate to the color centers. Some color centers (e.g., negatively-charged nitrogen vacancies) could exhibit a spectral shift as a function of temperature, allowing a determined frequency of a peak in a determined ODMR spectrum to allow for a determination of the temperature of the nanodiamonds containing the color centers. Oscillating electromagnetic fields could cause heating of magnetic nanoparticles, leading to localized heating of regions proximate to the heated magnetic nanoparticles. The location of magnetic nanoparticles proximate to color centers in nanodiamond could thus be detected by detecting changes in temperature corresponding to changes of amplitude of the oscillating magnetic fields. Other methods, including methods employed in magnetic resonance imaging or nuclear magnetic resonance imaging, could be employed to detect one or more properties of color centers in nanodiamonds and/or of the environment of the color centers The nanodiamonds and magnetic nanoparticles of the imaging agent can be functionalized by covalently or otherwise attaching or associating a bioreceptor that specifically binds or otherwise interacts with a particular analyte or portion of a particular analyte. The bioreceptor can be an antibody, peptide, nucleic acid, phage, bacteria, virus, aptamer or any other molecule with a defined affinity for a target analyte. Other compounds or molecules, such as fluorophores or autofluorescent or luminescent markers or non-optical contrast agents (e.g. acoustic impedance contrast, RF contrast and the like), which may assist in interrogating the nanodiamonds and/or magnetic nanoparticles may also be attached to the nanodiamonds and/or magnetic nanoparticles.

The imaging agent could include nanoparticles that include other elements in addition to the functionalized nanodiamonds and functionalized magnetic nanoparticles as described herein. Those of skill in the art will understand a "particle" in its broadest sense and that it may take the form of any fabricated material, a molecule, tryptophan, a conductive or nonconductive nanorod, a quantum dot, a virus, a phage, a complex of nanodiamonds, etc. Further, a particle may be of any shape, for example, spheres, rods, non-symmetrical shapes, etc.

A system may include one or more data collection systems for interrogating, in a non-invasive manner, functionalized nanodiamonds and functionalized magnetic particles present in an environment, such as a lumen of subsurface vasculature in a particular local area of a human. In some examples, the system may include an interrogating light source for transmitting illumination that can penetrate into a portion of subsurface vasculature, or another environment, and a light sensor for detecting an emitted light that is emitted by color centers in functionalized nanodiamonds in the portion of subsurface vasculature, or other environment, in response to the illumination. The emitted light can have one or more properties that are dependent on the magnetic field in the environment of the color centers, such that the location of magnetic nanoparticles proximate to the color centers can be determined using the detected one or more properties of the emitted light. The system may also include an electromagnetic field emitter configured to emit a static or dynamic electromagnetic field to enable, modulate, or otherwise affect the dependence of the one or more properties of the emitted light on the magnetic field in the environment of the color centers. The electromagnetic filed emitter may be configured to emit one or more of magnetic fields, radiofrequency electromagnetic radiation, microwave radiation, or some other directed electric or magnetic phenomenon.

The above described system may be implemented as a wearable device. The term "wearable device," as used in this disclosure, refers to any device that is capable of being worn at, on, or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The light sensor, light source, and, in some examples, a processor and/or electromagnetic field emitter, may be provided on the wearable device. In other embodiments, the above described system may be implemented as a stationary measurement device to which a user may be brought into contact or proximity with or as a device that may be temporarily placed or held against a body surface during one or more measurement periods. In other embodiments, the above described system may be implemented to interrogate an environment that is not a part of a human body, e.g., an in vitro or other sample container, an outdoor environment, an animal body, or some other environment of interest containing functionalized nanodiamonds and functionalized magnetic nanoparticles.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Imaging Agents

In some examples, information about analytes in an environment can be obtained by detecting properties of an imaging agent, for example, functionalized color-center-containing nanodiamonds and functionalized magnetic particles as described herein. Color centers in nanodiamond can emit light in response to illumination of the color centers; further, one or more properties of the emitted light could be related to a magnetic field, electromagnetic oscillation, or other effect caused by a magnetic particle proximate to the color centers. Nanodiamonds and magnetic particles could be functionalized (i.e., attached to one or more bioreceptors) in such a way that the presence of one or more analytes in the environment could cause the functionalized nanodiamonds and functionalized magnetic particles to be more proximate, more likely to be proximate and/or to have some other relationship that is detectable by illuminating the color center(s) of the functionalized nanodiamonds.

The functionalized nanodiamonds can include a variety of color centers. Color centers include dopants that can emit light in response to illumination of the dopants. Color centers can have specific optical properties that make them useful for imaging or use in imaging agents; for example, color centers in nanodiamonds can have narrow light emission spectra. Color center dopants can include a variety of carbon and non-carbon atoms, a variety of crystal defects, and combinations of atoms and defects. For example, a color center in a nanodiamond could include a negatively-charged, positively-charged, multiply-charged, or neutral silicon or nitrogen vacancy center. Individual nanodiamonds could include single color centers or could include populations of color centers. In some examples, the color centers could have orientation-specific properties. For example, negatively-charged nitrogen vacancy centers could be sensitive to magnetic fields parallel to a direction of the nitrogen vacancy center, but substantially insensitive to magnetic fields perpendicular to the direction of the nitrogen vacancy center. A population of color centers in an individual nanodiamond could be randomly oriented, could have a common orientation, or could have some other relationship between the orientations of respective individual color centers of the population of color centers.

Color centers in a nanodiamond could include negatively charged nitrogen vacancy centers. Negatively-charged nitrogen vacancy centers in diamond (NV centers) can be characterized by emission of light having a band of wavelengths between approximately 650 and 800 nanometers. This emission can occur in response to illumination having any wavelength in a range of wavelengths, for example, from about 500 nanometers to about 650 nanometers. Color centers in nanodiamond could additionally or alternatively include negatively-charged centers, positively-charged centers, neutral centers, or multiply-charged centers. Color centers having different charge states can have different respective optical properties. Further, color centers in diamond could additionally or alternatively include other dopants, including silicon, carbon, nickel, or other elements.

Nanodiamonds may be produced by a variety of methods and may assume a variety of morphologies. In some examples, nanodiamonds are produced by detonation (detonation nanodiamonds, DNDs) of explosives. In these examples, color centers can be created in the DNDs by inclusions of dopant atoms and precursor chemicals within the mix of explosives used to create the nanodiamonds. In some examples, nanodiamonds are created through chemical vapor deposition (CVD) or physical vapor deposition (PVD) and color centers or other properties of the nanodiamonds are controlled by controlling properties of the CVD, PVD, or other processes used to create the nanodiamonds. Additionally or alternatively, dopants (including dopant atoms, dopant crystal defects, and other dopants) can be added to nanodiamonds after the creation of the nanodiamonds, for example, by exposing the nanodiamonds to an ion beam. Creation of a desired color center or population of color centers in a nanodiamond can include other processes, for example, an annealing process following exposure to an ion beam or following some other process. Additional methods of fabricating doped, functionalized, color-center-containing nanodiamonds are anticipated.

Functionalized nanodiamonds as described herein could be polycrystalline. That is, the nanodiamonds can comprise a plurality of crystal domains. Additionally or alternatively, an individual functionalized nanodiamond could include a monocrystalline nanodiamond. In some examples, nanodiamonds can have sizes between approximately 5 nanometers and 5 micrometers. For example, an imaging agent can include functionalized nanodiamonds having a mean size of approximately 35 nanometers. In some examples, the size of the nanodiamonds could be chosen such that magnetic resonance peak of color centers in the nanodiamonds was sufficiently narrow to enable some application. For example, the nanodiamonds could be between 10 and 100 nanometers in diameter Optical properties of color centers in diamond could be related to static and/or changing magnetic fields in the environment of the color centers. For example, a fluorescence intensity of the color centers could be changed by the presence in the environment of the color centers of electromagnetic energy of one or more specific frequencies. Static magnetic fields could cause a change in the number, relative energy, or other properties of allowed spin or other quantum states of the color centers. Time-carrying magnetic fields could cause a change in the occupancy of spin or other quantum states of the color centers by having a frequency corresponding to an energy difference between two or more spin or other quantum states of the color centers.

An optical property of a color center could be dependent upon the occupancy of the two or more spin or other quantum states of the color centers. For example, certain spin or other quantum states of a color center, when occupied, could be more likely to result in emission of a fluorescent photon when the color center is illuminated than other states of the color center. Thus, an overall fluorescence intensity of a color center could be related to the occupancy of spin or other quantum states of the color center, and thus the overall fluorescence intensity of the color center could be related to static and/or changing magnetic fields in the environment of the color center. Further, an overall fluorescence intensity of a population of color centers (e.g., a population of color centers contained in a functionalized nanodiamond) could be related to static and/or changing magnetic fields in the environment of the population of color centers. Additionally, the occupancy of two or more spin or other quantum states of the color centers could be affected by absorption of light energy by the color centers. For example, illumination of color centers by illumination having a certain wavelength could 'polarize' the spin or other quantum states of the color centers; that is, illumination could cause one states of a set of two or more states to be preferentially occupied.

An example of spin states and transitions between said states for a negatively-charged nitrogen vacancy color center (NV$^-$ center) in diamond is illustrated in FIG. 1A. The energy diagram 100a shows higher-energy states as vertically above lower-energy states. Thus, first 110 and second 115a spin states have lower energy than excited states 120. Further, the first energy diagram 100a illustrates states for a NV$^-$ center in an environment having substantially no magnetic field parallel to the z-axis of the NV$^-$ center. The first state 110 has a spin of zero, and the second state 115a has nonzero spin. The first 110 and second 115a states are separated by an energy difference of approximately 2.869 GHz when the NV$^-$ center has a temperature substantially equal to room temperature.

Photon absorption transitions 140 illustrate transitions from the first 110 and second 115a states to corresponding excited states 120 caused by the NV$^-$ center absorbing a photon having an appropriate wavelength (between approximately 500 to 650 nanometers). Photon emission transitions 150 illustrate transitions from excited states 120 to the first 110 and second 115a states accompanied by the NV$^-$ center emitting a fluorescent photon having a wavelength between approximately 650-800 nanometers.

Alternatively, NV– centers can experience a first non-radiative transition 160 from the excited state 120 to a dark state 130. The NV– centers can then experience a second non-radiative transition 170 from the dark state 130 to the first state 110. When the NV– center is in the first state 110 and absorbs a photon (transition 140), it is more likely to emit a fluorescent photon (transition 150) than if the NV$^-$ center is in the second state 115a. As a result, illumination of the NV⁻ center with light of an appropriate wavelength (between approximately 500 to 650 nanometers) can polarize the states of the NV⁻ center, i.e., cause the NV⁻ center to occupy the first state 110 rather than occupy some steady-state superposition of the first 110 and second 120 states.

Factors of the environment of the NV– center (e.g., thermal vibrations due to nonzero temperature, electromagnetic oscillations of an appropriate frequency (e.g., approximately 2.869 GHz at room temperature)) can cause the occupancy of the first 110 and second 120 states of the NV– center to change from being polarized to being some superposition of the first 110 and second 120 states. As a result, a current occupancy state of the first 110 and second 120 states of the NV– center could be related to past occupancy states of the first 110 and second 120 states and to illumination or other energy in the environment of the NV– center. Further, the current occupancy state of the first 110 and second 120 states of the NV– center could be detected by illuminating the NV– center and detecting a fluorescence intensity of the color center that is related to the current occupancy state of the first 110 and second 120 states.

Figure 1B:
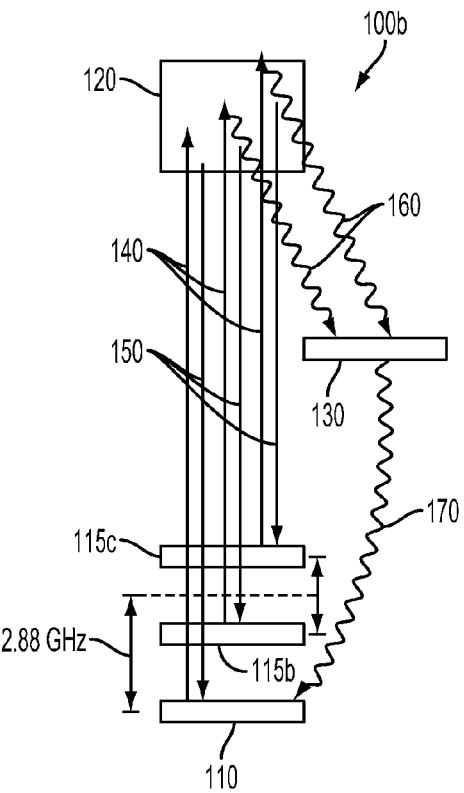
FIG. 1B is an energy diagram of an example color center in a magnetic field.

An example of spin states and transitions between states for the negatively-NV⁻ center when the NV– center is exposed to a DC magnetic field is illustrated in FIG. 1B. A second energy diagram 100b shows the first spin state 110 and the excited states 120. Additionally, the second energy diagram 100b shows third 115b and fourth 115c spin states. The third 115b and fourth 115c states have spins with magnitude equal to 1 and direction parallel and anti-parallel, respectively, to the direction of the DC magnetic field parallel to the z-axis of the NV⁻ center. The third 115b and fourth 115c states represent a splitting of the second state 115a due to the presence of the DC magnetic field (e.g., due to Zeeman splitting). The third 115b and fourth 115c states are separated by an energy difference related to the magnitude of the DC magnetic field parallel to the z-axis of the NV⁻ center. Further, the first state 110 and a mean energy level of the third 115b and fourth 115d states are separated by an energy difference of approximately 2.869 GHz when the NV⁻ center has a temperature substantially equal to room temperature.

Photon absorption transitions 140 illustrate transitions from the first 110, third 115b, and fourth 115d states to corresponding excited states 120 caused by the NV⁻ center absorbing a photon having an appropriate wavelength (between approximately 500 to 650 nanometers). Photon emission transitions 150 illustrate transitions from excited states 120 to the first 110, third 115b, and fourth 115d states accompanied by the NV⁻ center emitting a fluorescent photon having a wavelength between approximately 650-800 nanometers. Similarly to the scenario illustrated by the first energy diagram 100a, NV– centers can alternatively experience the first non-radiative transition 160 from the excited state 120 to the dark state 130. The NV– centers can then experience the second non-radiative transition 170 from the dark state 130 to the first state 110.

When the NV– center is in the first state 210 and absorbs a photon (transition 140), it is more likely to emit a fluorescent photon (transition 150) than if the NV– center is in the third 115b or fourth 115d states. As a result, illumination of the NV– center with light of an appropriate wavelength (between approximately 500 to 650 nanometers) can polarize the states of the NV– center, i.e., cause the NV– center to occupy the first state 110 rather than occupy some steady-state superposition of the first 110, third 115b, and fourth 115d states. Also similarly to the scenario illustrated by the first energy diagram 100a, factors of the environment of the NV– center (e.g., thermal vibrations due to nonzero temperature, electromagnetic oscillations of an appropriate frequency) can cause the occupancy of the first 110, third 115b, and fourth 115d states of the NV– center to change from being polarized to being some superposition of the first 110, third 115b, and fourth 115d states.

The relative energies of allowed energy states of a color center could be determined from a magnetic resonance spectrum of the color center. A magnetic resonance spectrum is a record of a property of the color center (e.g., a fluorescence intensity of the color center) determined and/or detected when the color center is being exposed to electromagnetic radiation having a range of frequencies.

Figure 1C:
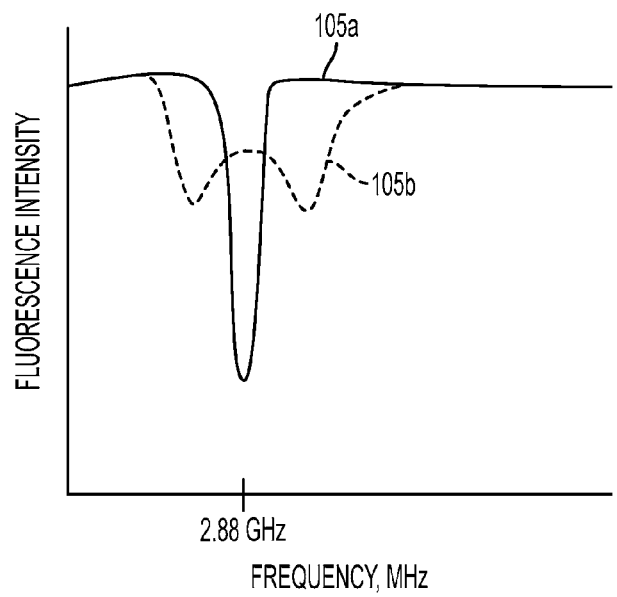
FIG. 1C illustrates example magnetic resonance spectra of the example color centers of FIG. 1A and FIG. 1B.

FIG. 1C illustrates magnetic resonance spectra for the scenarios illustrated in FIGS. 1A and 1B (i.e., for a NV– center at room temperature and exposed to a magnetic field having substantially zero magnitude in a direction parallel to the z-axis of the NV⁻ center (FIG. 1A) or exposed to a magnetic field having nonzero magnitude in a direction parallel to the z-axis of the NV⁻ center (FIG. 1B). First 105a and second 105b illustrated example spectra show the fluorescence intensity of a NV– center when exposed to microwave energy having a range of frequencies in the zero-magnitude (1A) and nonzero-magnitude (1B) magnetic field scenarios, respectively. The first spectrum 105a shows a single inverted peak corresponding to a drop in overall fluorescence of the NV– center when exposed to microwave energy having a frequency approximately equal to 2.869 GHz, the energy difference between the first 110 and second 115a spin states. The second spectrum 105b shows an inhomogeneously broadened inverted peak corresponding to a drop in overall fluorescence of the NV– center when exposed to microwave energy having a frequency approximately equal to energy difference between the first 110 and third 115b or first 110 and fourth 115d spin states.

The magnetic resonance spectrum of a color center could be determined and/or detected by a number of methods. The magnetic resonance spectrum could be determined optically (i.e., an optically detected resonance spectrum (ODMR) could be determined) by illuminating the color center and detecting an amplitude or other property of fluorescent light emitted from the color center in response to the illumination when the color center is exposed to electromagnetic radiation having a range of frequencies (e.g., a range spanning frequencies corresponding to differences in energy between allowed spin or other quantum states of the color center). Additionally or alternatively, the occupancy of spin or other quantum states of the color center could be polarized or otherwise affected by illumination during a first period of time, and the change in the occupancy of the state over time due to exposure to electromagnetic radiation having a specified frequency could be detected during a second period of time by illuminating the color center and detecting an amplitude or other property of fluorescent light emitted from the color center in response to the illumination during the second period of time.

The ODMR could be wholly determined (by detecting the amplitude or other property of the emitted fluorescent light when the color center is exposed to electromagnetic radiation having a number of closely-spaced frequencies). Alternatively, the ODMR could be partially determined, by detecting the amplitude or other property of the emitted fluorescent light when the color center is exposed to electromagnetic radiation having two or more specified frequencies. For example, a fluorescence intensity of the color center could be detected when the color center is exposed to electromagnetic radiation having two or more specified frequencies such that one or more features of the magnetic resonance spectrum of the color center could be determined. For example, a center frequency of a peak of the spectrum (corresponding to an energy difference between allowed states of the color center), or a width and/or broadening of a peak of the spectrum, could be determined by detecting the fluorescence intensity of the color center when exposed to electromagnetic radiation having two or more specified frequencies.

Further, the determined one or more features of the spectrum could be related to properties of the environment of the color center and could be used to determine the properties of the environment of the color center. The direction and/or magnitude of electric and/or magnetic fields, the magnitude and/or spectral content of electromagnetic noise, temperature, pH, mechanical strain in the diamond lattice containing the color center, or other properties of the environment of the color center could be related to one or more features or changes of features of the magnetic resonance spectrum of the color center.

Additionally or alternatively, other techniques could be used to optically detect properties of the environment of one or more color centers in functionalized nanodiamonds as described herein. For example, techniques from nuclear magnetic resonance spectroscopy or magnetic resonance imaging (e.g., the application of spin-manipulating pulses of electromagnetic energy (e.g., spin-locking, pi and half-pi pulses, XY-N pulse sequences)) could be employed to manipulate properties (e.g., spin direction, occupancy of spin or other quantum states) of the color center such that the altered properties reflect one or more properties of the environment of the color center and such that the altered properties can be detected optically. For example, XY-2N pulse sequences having specified timings could be applied to the color center such that the color center is made sensitive to time-varying magnetic fields of a specified range of frequencies related to the specified timings. In this way, the color center could be used to detect one or more properties of time-varying magnetic fields in the environment of the color center (e.g., to wholly or partially determine an energy spectrum of electromagnetic noise in the environment of the color center).

Note that negatively charged nitrogen vacancy color centers (NV− centers) are used herein as an illustrative example of a color center that could be contained in a functionalized nanodiamond to enable the embodiments described herein. Alternate color centers in diamond are anticipated (e.g., silicon-vacancy color centers, nickel-containing color centers, silicon-carbon color centers). Alternate color centers have an optical property (e.g., a fluorescence intensity, a property of light emitted by the color centers in response to illumination) that is related to one or more properties of the environment of the color centers (e.g., a DC magnetic field, a time-varying magnetic field, a temperature) such that the proximity of the color centers to a nearby functionalized magnetic particle can be detected and/or determined by detecting the optical property of the color centers. In some examples, the color center could have an occupancy state of spin or other quantum states of the color center that was affected by the magnetic property of the environment; further, the occupancy state could be related to an optical property of the color center. In some examples, the occupancy state could be polarized or otherwise altered by being illuminated having a wavelength in a specified range.

Functionalized nanodiamonds containing color centers (as described herein) could be used to detect the proximity of functionalized magnetic particles to the functionalized nanodiamonds. A functionalized magnetic particle could cause a change in a magnetic property of the environment proximate to the functionalized magnetic particle. This change could be detected by functionalized nanodiamonds proximate to the functionalized magnetic particle.

In some examples, the functionalized magnetic particle could produce a DC magnetic field, and a functionalized nanodiamond proximate to the functionalized magnetic particle could be used to detect the DC magnetic field. In some examples, rotation of the functionalized magnetic particle or a rotation or other change in a magnetic dipole moment of the functionalized magnetic particle could produce a time-varying magnetic field, and a functionalized nanodiamond proximate to the functionalized magnetic particle could be used to detect one or more properties of the time-varying magnetic field.

The functionalized magnetic particles could include one or more particles of a magnetic material. The magnetic material could be a ferromagnetic, ferrimagnetic, paramagnetic, superparamagnetic, or other material having one or more magnetic properties sufficient to create a DC and/or time-varying magnetic field in an environment proximate to the magnetic material. In some examples, the magnetic material of the magnetic particle has a small size such that the magnetic particle has a single magnetic domain. In some examples, the functionalized magnetic particle could include a particle of superparamagnetic iron oxide. In some examples, one or more properties of the DC and/or time-varying magnetic field created by the functionalized magnetic particle are related to one or more properties of the functionalized magnetic particle. For example, the magnitude of a dipole moment of the functionalized magnetic particle could be related to the volume and/or geometry of the functionalized magnetic particle. For example, an energy spectrum of a time-varying magnetic field created by the functionalized magnetic particle could be related to a diameter of the functionalized magnetic particle and/or a drag coefficient of the magnetic particle.

The bioreceptors of the functionalized nanodiamonds and functionalized magnetic particles can be designed to selectively bind or otherwise recognize a particular analyte or set analytes. For example, the bioreceptors can include a variety of structures, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The bioreceptors (or a combination of bioreceptors) could be chosen to cause the functionalized nanodiamonds and/or functionalized magnetic particles to selectively interact with an analyte that includes a target or targets of the bioreceptors. For example, the bioreceptor could be a bioreceptor that selectively interacts with a protein or other element that is expressed by cancer cells to enable the use of the contrast agent (i.e., the functionalized nanodiamonds and the functionalized magnetic particles) to detect cancer cells.

The functionalized nanodiamonds and the functionalized magnetic particles can be introduced into a variety of environments by a variety of methods. For example, the functionalized nanodiamonds and the functionalized magnetic particles can be introduced into a person's blood stream by injection, ingestion, inhalation, transdermally, or in some other manner.

Nanodiamonds and/or magnetic particles can be functionalized by attaching bioreceptors to the nanodiamonds and/or magnetic particles using a variety of methods. Bioreceptors can be attached to the surface of the nanodiamonds and/or magnetic particles by covalent bonds, adsorption, electrostatic attraction, Van der Waals forces, or by some other mechanism. The surface of the nanodiamonds and/or magnetic particles could be treated or altered to facilitate binding of bioreceptors. In some examples, the surface of the nanodiamonds could be altered such that the diamond lattice is terminated in carboxyl groups. In some examples, the surface of the nanodiamonds could be treated with a strong oxidative acid.

Additionally or alternatively, a coating or other substance could contain the nanodiamonds and/or magnetic particles, be bound to the surface of the nanodiamonds and/or magnetic particles, or otherwise attach to the nanodiamonds and/or magnetic particles such that bioreceptors can be attached to the coating or other substance, such that the bioreceptor is indirectly attached to the nanodiamonds and/or magnetic particles. More than one bioreceptor could be attached to the nanodiamonds and/or magnetic particles. In some examples, complexes of the same or different bioreceptors could be attached directly or indirectly to the nanodiamonds and/or magnetic particles such that the nanodiamonds and/or magnetic particles more selectively interacted with a target analyte or target portion of a target analyte.

Functionalized nanodiamonds and functionalized magnetic particles in an environment that does not contain an analyte of interest could generally be randomly distributed in the environment. That is, the proximity between an individual functionalized nanodiamond and one or more of the functionalized magnetic particles could be a random value having a distribution related to the concentration of the functionalized nanoparticles and the functionalized magnetic particles in the environment. For example, the proximity could be more likely to be increased and/or more functionalized magnetic particles are likely to be proximate to an individual functionalized nanodiamond when the concentration of one or both of the functionalized nanoparticles and the functionalized magnetic particles is increased.

When the environment contains the analyte, and the functionalized nanodiamonds and functionalized magnetic particles are configured to selectively interact with (e.g., 'bind' to) the analyte, an individual nanodiamond that is bound to the analyte could be more likely to be proximate to one or more functionalized magnetic particles that are also bound to the analyte. Thus, the detection and/or determination that an individual functionalized nanodiamond is proximate to one or more functionalized magnetic particles could be used to determine that the individual nanodiamond was bound to, proximate to, or otherwise interacting with the analyte.

The proximity (i.e., maximum distance) between an individual functionalized nanodiamond and functionalized magnetic particles sufficient to allow the proximity to be detected could be related to properties of the functionalized nanodiamonds and functionalized magnetic particles, properties of the environment, and/or the method used to detect the proximity. Additionally or alternatively, a property of the proximity between the individual functionalized nanodiamonds and the functionalized magnetic particles (e.g., a distance between the individual functionalized nanodiamonds and a functionalized magnetic particle) and/or a property of the functionalized magnetic particles (e.g., a size of the particles) could be detected.

Figure 2A:
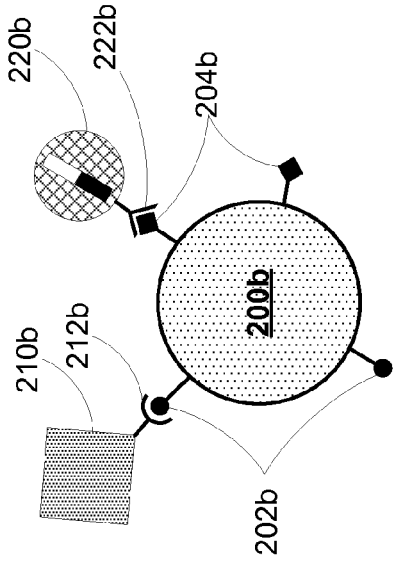
FIG. 2A is an illustration of example functionalized particles in an environment.

FIG. 2A illustrates an example of a functionalized nanodiamond and a functionalized magnetic particle selectively interacting with an analyte 200a, such that the functionalized nanodiamond and the functionalized magnetic particle are proximate and such that the proximity is related to the interaction of the functionalized nanodiamond and the functionalized magnetic particle with the analyte 200a. The analyte 200a includes a number of unique ligands 202a that are specific to the analyte 200a; that is, a bioreceptor or other element configured to selectively interact with the unique ligands 202a will selectively interact with the analyte 200a. The functionalized nanodiamond includes a nanodiamond 210a attached to a first bioreceptor 212a. The functionalized magnetic particle includes magnetic element 220a attached to a second bioreceptor 222a. The first 212a and second 222a bioreceptors are configured to selectively interact with (e.g., 'bind' to) the ligands 202a of the analyte 200a. The magnetic element 220a has one or more magnetic properties (e.g., a magnetic dipole moment, susceptibility to heating by oscillating electromagnetic fields) such that the proximity between the magnetic element 220a and color centers contained in the nanodiamond 210a can be detected by at least illuminating the color centers and detecting one or more properties of a light emitted by the color centers. The first 212a and second 222a bioreceptors could be the same bioreceptor or could be different bioreceptors configured to selectively interact with the ligands 202a.

Figure 2B:
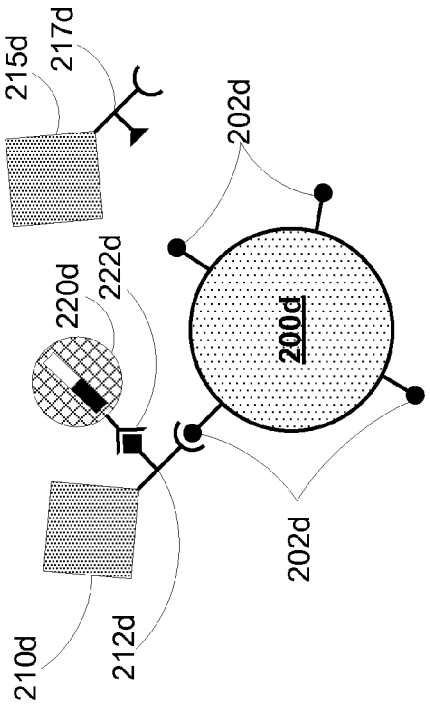
FIG. 2B is an illustration of example functionalized particles in an environment.

An analyte in an environment could be uniquely identified by a specific combination of ligands or other elements that are, individually, not specific to the analyte. FIG. 2B illustrates an example of a functionalized nanodiamond and a functionalized magnetic particle selectively interacting with an analyte 200b, such that the functionalized nanodiamond and the functionalized magnetic particle are proximate and such that the proximity is related to the interaction of the functionalized nanodiamond and the functionalized magnetic particle with the analyte 200b. The analyte 200b includes a number of first ligands 202b and second ligands 204b that may be individually expressed by other elements of the environment of the analyte 200b. However, the expression of both the first 202b and second 204b ligands is specific to the analyte 200b. The functionalized nanodiamond includes a nanodiamond 210b attached to a first bioreceptor 212b. The functionalized magnetic particle includes magnetic element 220b attached to a second bioreceptor 222b. The first 212b and second 222b bioreceptors are configured to selectively interact with (e.g., 'bind' to) the first 202b and second 204b ligands of the analyte 200b, respectively. The magnetic element 220b has one or more magnetic properties (e.g., a magnetic dipole moment, susceptibility to heating by oscillating electromagnetic fields) such that the proximity between the magnetic element 220b and color centers contained in the nanodiamond 210b can be detected by at least illuminating the color centers and detecting one or more properties of a light emitted by the color centers.

Additionally or alternatively, the combination of the first 202b and second 204b ligands could be common to other elements of the environment than the analyte 200b, and a relative location or other properties of the first 202b and second 204b ligands of the analyte 200b could be specific to the analyte 200b and enable detection of the analyte 200b using the functionalized nanodiamond and the functionalized magnetic particle. For example, the first 202b and second 204b ligands could have a first characteristic proximity on the analyte 200b (i.e., the first 202b and second 204b ligands could be separated by a characteristic distance when expressed on the analyte 200b) and a different characteristic proximity when present on or in other elements of the environment. The detection and/or determination that the first 202b and second 204b ligands have a proximity substantially equal to the first characteristic proximity could be used to determine that the functionalized nanodiamond is bound to, proximate to, or otherwise interacting with the analyte 200b. In some examples, the first 202b and second 204b ligands could have a characteristic relative orientation on the analyte 200b.

Figure 2C:
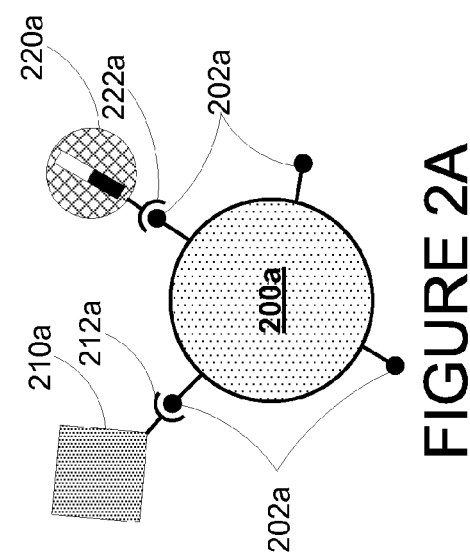
FIG. 2C is an illustration of example functionalized particles in an environment.

An analyte in an environment could be uniquely identified by a specific ligand or other elements that are specific to the analyte and that specifically interact with a functionalized nanodiamond and/or functionalized magnetic particle based on a specific interaction with some other functionalized nanodiamond and/or functionalized magnetic particle. FIG. 2C illustrates an example of a functionalized nanodiamond and a functionalized magnetic particle selectively interacting with an analyte 200c, such that the functionalized nanodiamond and the functionalized magnetic particle are proximate and such that the proximity is related to the interaction of the functionalized nanodiamond and the functionalized magnetic particle with the analyte 200c. The analyte 200c includes a number of ligands 202c, 203c that are specific to the analyte 200c. The functionalized nanodiamond includes a nanodiamond 210c attached to a first bioreceptor 212c. The functionalized magnetic particle includes magnetic element 220c attached to a second bioreceptor 222c. The first bioreceptor 212c is configured to selectively interact with (e.g., 'bind' to) a first binding site of the ligands 202c, 203c (illustrated as circles in FIG. 2C). The ligands 202c, 203c additionally include a second binding site that has a configuration related to whether the first bioreceptor 212c is bound to the first binding site (illustrated as triangles on the un-bound ligands 202c and a square on the bound ligand 203c). The second bioreceptor 222c is configured to bind to the second binding site of the ligand 202c, 203c when the first bioreceptor 212c is bound to the first binding site of the ligand 202c, 203c. The magnetic element 220c has one or more magnetic properties (e.g., a magnetic dipole moment, susceptibility to heating by oscillating electromagnetic fields) such that the proximity between the magnetic element 220c and color centers contained in the nanodiamond 210c can be detected by at least illuminating the color centers and detecting one or more properties of a light emitted by the color centers.

The first 212c and second 222c bioreceptors could be the same bioreceptor or could be different bioreceptors configured to selectively interact with binding sites of the ligands 202c, 203c. Further, the first bioreceptor 212c being configured to bind to first binding site of the ligand 202c, 203c and to cause the change in the second binding site and the second bioreceptor 222c being configured to bind to the second binding site when the first bioreceptor 212c is bound to the first binding site is intended as an example; in some examples, the second bioreceptor 222c could be configured to bind to the first binding site and the first bioreceptor 212c could be configured to bind to the second binding site when the second bioreceptor 222c is bound to the first binding site.

Figure 2D:
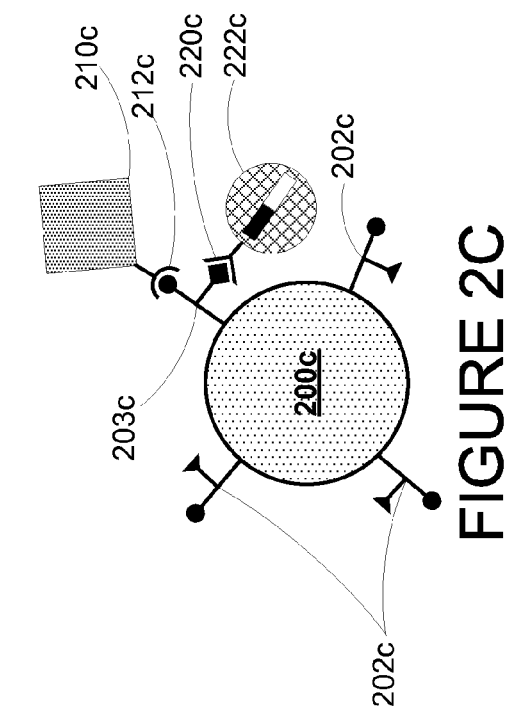
FIG. 2D is an illustration of example functionalized particles in an environment.

Functionalized nanodiamonds and/or functionalized magnetic particles could be configured to selectively interact with an analyte by selectively binding together when bound to, proximate to, or otherwise selectively interacting with the analyte. FIG. 2D illustrates an example of a functionalized nanodiamond and a functionalized magnetic particle selectively interacting with an analyte 200d, such that the functionalized nanodiamond and the functionalized magnetic particle are proximate and such that the proximity is related to the interaction of the functionalized nanodiamond and the functionalized magnetic particle with the analyte 200d.

The analyte 200d includes a number of unique ligands 202d that are specific to the analyte 200d; that is, a bioreceptor or other element configured to selectively interact with the unique ligands 202d will selectively interact with the analyte 200d. A first functionalized nanodiamond includes a first nanodiamond 210d attached to a first bioreceptor 212d. The functionalized magnetic particle includes magnetic element 220d attached to a second bioreceptor 222d. The first bioreceptor 212d is configured to selectively interact with (e.g., 'bind' to) the ligands 202d. The first bioreceptor 212d additionally include a binding site that has a configuration related to whether the first bioreceptor 212c is bound to the ligand 202d (illustrated as a square on the bound first bioreceptor 212d as a triangle on an un-bound third bioreceptor 217dc attached to a second nanodiamond 215d). The second bioreceptor 222d is configured to bind to the binding site of the first bioreceptor 212d when the first bioreceptor 212d is bound to the ligand 202d. Thus, the functionalized magnetic particle could be considered to be selectively interacting with the analyte 200d through elements of the functionalized nanodiamond (210d, 212d) that is selectively interacting with the analyte 200d. The magnetic element 220d has one or more magnetic properties (e.g., a magnetic dipole moment, susceptibility to heating by oscillating electromagnetic fields) such that the proximity between the magnetic element 220d and color centers contained in the nanodiamond 210d can be detected by at least illuminating the color centers and detecting one or more properties of a light emitted by the color centers.

Note that the first bioreceptor 212d being configured to bind to the ligand 202d and the second bioreceptor 222d being configured to bind to the binding site of the first bioreceptor 212d when the first bioreceptor 212d is bound to ligand 202d is intended as an example; in some examples, the second bioreceptor 222d could be configured to bind to the ligand 202d and a the first bioreceptor 212d could be configured to bind to a binding site on the second bioreceptor 222d when the second bioreceptor 222d is bound to the ligand 202d. Elements, receptors, and techniques from various sandwich assays, ELISA, or other analyte-detection methods wherein a first element selectively binds to an analyte and a second element binds to the first element when the first element is bound to the analyte could be applied to the embodiments described herein. In some examples, a number of functionalized nanodiamonds could be configured to selectively interact with a number of respective analytes, and a single type of functionalized magnetic particle could be configured to selectively interact with functionalized nanodiamonds that are selectively interacting with respective analytes. Conversely, a number of functionalized magnetic particles could be configured to selectively interact with a number of respective analytes, and a single type of functionalized nanodiamond could be configured to selectively interact with functionalized magnetic particles that are selectively interacting with respective analytes.

Functionalized nanodiamonds and/or functionalized magnetic particles as described herein may additionally include other elements. Functionalized nanodiamonds and/or functionalized magnetic particles could include biodegradable or non-biodegradable materials. For example, the functionalized magnetic particles may include polystyrene. Functionalized nanodiamonds and/or functionalized magnetic particles that include non-biodegradable materials may be provided with a removal means to prevent harmful buildup in the body or other environment. Generally, the functionalized nanodiamonds and/or functionalized magnetic particles may be designed to have a long half-life so that they remain in the vasculature, body fluids, or other environment to enable their use in detecting analytes over an extended period of time. Depending on the lifetime of the functionalized nanodiamonds and/or functionalized magnetic particles, however, new batches of functionalized nanodiamonds and/or functionalized magnetic particles may be periodically introduced into the environment.

An imaging agent could include a plurality of types of functionalized nanodiamonds and/or functionalized magnetic particles functionalized to selectively interact with respective analytes in an environment. For example, an imaging agent could include a first set of functionalized nanodiamonds functionalized to selectively interact with a first analyte and a second set of functionalized nanodiamonds functionalized to selectively interact with a second analyte, where the where the first set of functionalized nanodiamonds was detectably different from the second set (e.g., by containing a different type of color center, by containing a different ratio of concentrations of different types of color centers, or by some other method). Such an imaging agent could additionally include first and second sets of functionalized magnetic particles configured to selectively interact with the first and second analytes, respectively. Additionally or alternatively, an imaging agent could include more than one type of functionalized nanodiamonds and a single type of functionalized magnetic particles or a single type of functionalized nanodiamonds and more than one type of functionalized magnetic particles.

The analyte could be a clinically-relevant analyte. A clinically-relevant analyte could be any analyte that, when present or absent, or present at a particular concentration or range of concentrations, may be indicative of a medical condition or indicative that a medical condition may be imminent. For example, the clinically-relevant analyte could be an enzyme, hormone, protein, cell, or other biological element. In one relevant example, certain protein biomarkers expressed by a cell are known to be predictive of the cell being a cancer cell. By providing engineered particles functionalized with a bioreceptor that will selectively bind to these target protein biomarkers, interaction with the engineered particles (e.g., illuminating the particles, detecting properties of energy emitted by the particles, and/or generating a directed field to orient the engineered particles) could be used to determine one or more properties of the cell (e.g., the location of the cell, whether the cell was being transported by blood in a lumen of subsurface vasculature of a person's body, that the cell was a cancer cell).

The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, a, or some other environment. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., functionalized nanodiamonds and functionalized magnetic particles) to the environment.

In some examples, one or both of the functionalized nanodiamonds and functionalized magnetic particles could be a part of the environment. For example, the functionalized magnetic particle could be an enzyme or other element that existed as part of a human body and that contained a magnetic moiety. In some examples, the color-center-containing nanodiamond and/or magnetic particle could be selectively absorbed by or otherwise incorporated into the analyte, rather than being functionalized to selectively bind to the analyte.

Those of skill in the art will understand the term "particle" in its broadest sense and that it may take the form of any fabricated material, a molecule, tryptophan, a virus, a phage, a nanodiamond, a nanorod, a quantum dot, a single-magnetic-domain crystal of a metal, etc. Functionalized nanodiamonds could be described as particles, or could be incorporated into particles including elements additional to the color-center-containing nanodiamonds and bioreceptors described herein. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies" on the order of 1-10 micrometers. In this arrangement, the assemblies could provide the signal strength of a larger particle, but would be deformable, thereby preventing blockages in smaller vessels and capillaries.

III. Illustrative Methods

Figure 3:
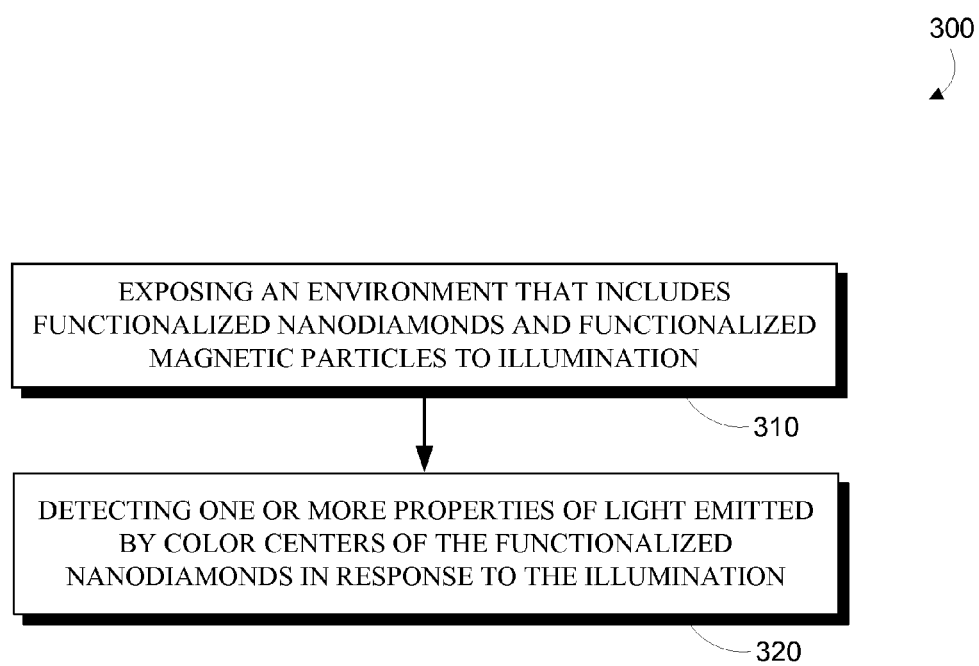
FIG. 3 is a flowchart of an example method.

FIG. 3 is a flowchart of a method 300 for detecting the presence, location, orientation, concentration, or other properties functionalized nanodiamonds, functionalized magnetic particles, and/or an analyte in an environment. Each functionalized nanodiamond and functionalized magnetic particle is configured to selectively interact with the analyte (e.g., by binding to one or more proteins, ligands, or other elements of the analyte). Each functionalized nanodiamond contains at least one color center configured to emit light in response to illumination of the at least one color center. Further, one or more properties of light emitted by individual color centers in response to illumination is related to proximity between the individual color centers and the functionalized magnetic particles.

The method 300 includes exposing the environment that includes the functionalized nanodiamonds and the magnetic particles to illumination 310. The illumination is such that color centers contained in the functionalized nanodiamonds absorb the illumination and emit light in response. This can include emitting illumination having a specific wavelength or spectral profile, such that the illumination can be absorbed by the color centers, emitted by the color centers, efficiently transmitted through the environment, or other considerations. Exposing the environment to illumination 310 can include emitting illumination having a specified amplitude, phase, polarization, or other property. Further, exposing the environment to illumination 310 can include emitting illumination having different properties at different points in time. For example, it could include emitting illumination having a first amplitude, wavelength, polarization, or other property at a first point in time and emitting illumination having a second amplitude, wavelength, polarization, or other property at a second point in time.

The method 300 additionally includes detecting one or more properties of the light emitted by the color centers of the functionalized nanodiamonds in response to the illumination 320. This can include detecting the amplitude, wavelength, degree of polarization, orientation of polarization, location, or other properties of the emitted light. It can also include detecting one or more properties of light emitted by the color centers of the functionalized nanodiamonds at more than one point in time. For example, the location and amplitude of light emitted by color centers in response to illumination could be detected at a plurality of points in time. The respective plurality of detected amplitudes and locations of emitted light could then be used to infer respective locations of and/or the occupancy of spin or other quantum states of color centers contained in functionalized nanodiamonds in the environment at the plurality of points in time.

The method 300 could include additional steps or elements in addition to exposing the environment to illumination 310 and detecting one or more properties of the energy emitted by the color centers of the functionalized nanodiamonds in response to the illumination 320. For example, the method 300 could include introducing the functionalized nanodiamonds and/or functionalized magnetic particles into the environment (e.g., injecting, ingesting, transdermally transferring, or otherwise introducing the engineered particles into a lumen of vasculature of a human, applying the engineered particles to an in vitro or other non-human biological environment, applying the engineered particles to a non-biological environment or other methods).

The method 300 could include determining that an individual functionalized nanodiamond is proximate to at least one magnetic particle based on the detected one or more properties of the light emitted by the color centers of the individual functionalized nanodiamond in response to illumination. In some examples, the method 300 could include determining the proximity of a functionalized magnetic particle to an individual functionalized nanodiamond by determining a rate at which the occupancy of spin or other quantum states of the color centers of the individual functionalized nanodiamond changes from a polarized state to an equilibrium state. In some examples, the method 300 could include determining the proximity of a functionalized magnetic particle to an individual functionalized nanodiamond by determining one or more features of a magnetic resonance spectrum of the color centers of the individual functionalized nanodiamond, where the determined one or more features are related to the proximity of the functionalized magnetic particle to the individual functionalized nanodiamond. Other methods of determining the proximity of a functionalized magnetic particle to an individual functionalized nanodiamond are described herein.

The method 300 could further include determining that an individual functionalized nanodiamond and at least one functionalized magnetic particle are bound to the analyte based on a determination that the individual functionalized nanodiamond is proximate to the at least one functionalized magnetic particle. For example, the determination that an individual nanodiamond was less than a certain distance from one or more magnetic particles could be used to determine that one or more instances of the analyte was proximate to the individual nanodiamond and at least one magnetic particle. This determination could be based on additional information; for example, it could be determined that one or more instances of the analyte was proximate to an individual nanodiamond and at least one magnetic particle if the proximity between the individual nanodiamond and the at least one magnetic particle was below a certain distance for a certain period of time. Other additional and/or alternative elements of method 300 are anticipated.

Figure 4:
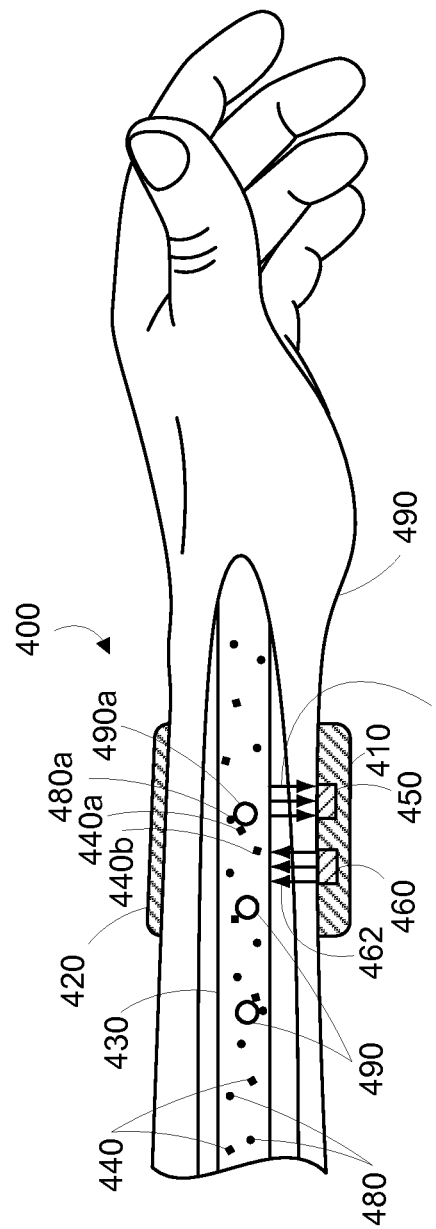
FIG. 4 is side partial cross-sectional view of an example wrist-mounted device, while on a human wrist.

FIG. 4 is a partial cross-sectional side view of a human wrist illustrating the operation of various examples of a wrist-mounted device. In the example shown in FIG. 4, the wrist-mounted device 400 includes a measurement platform 410 mounted on a strap or wristband 420 and oriented on the anterior side 490 of the wearer's wrist. Measurement platform 410 is positioned over a portion of the wrist where subsurface vasculature 430 is easily observable. Functionalized nanodiamonds 440 and functionalized magnetic particles 480 have been introduced into a lumen of the subsurface vasculature 430 by one of the means discussed above. Each functionalized nanodiamond 440 contains at least one color center configured to emit light in response to illumination of the at least one color center. Further, one or more properties of light emitted by individual color centers in response to illumination is related to proximity between the individual color centers and the functionalized magnetic particles 480. In this example, measurement platform 410 includes a data collection system having both a light sensor 450 and a light source 460. The functionalized nanodiamonds 440 and functionalized magnetic particles 480 are configured to selectively interact with (e.g., bind to) an analyte 490 in the subsurface vasculature.

The state of the subsurface vasculature 430 during detection is illustrated in FIG. 4. At this time, light source 460 is transmitting illumination 462 into the portion of subsurface vasculature 430 and light sensor 450 is detecting one or more properties of an emitted light 452 emitted by color centers in functionalized nanodiamonds 440 in response to the illumination 462. The emitted light 452 can have one or more properties related to proximity between an emitting color center and one or more functionalized magnetic particles 480.

Functionalized nanodiamonds 440 and functionalized magnetic particles 480 in the subsurface vasculature 430 that are not bound or otherwise selectively interacting with the analyte 490 can be less proximate to each other than functionalized nanodiamonds 440 and functionalized magnetic particles 480 that are bound or otherwise selectively interacting with the analyte 490. For example, a first individual functionalized nanodiamond 440*a* and an individual magnetic particle 480*a* are bound to an individual instance of the analyte 490*a*. Being bound to the individual instance of the analyte 490*a* maintains a proximity between the first individual functionalized nanodiamond 440*a* and the individual magnetic particle 480*a* within a certain low range of distances related to the size of the individual instance of the analyte 490*a*. A second individual functionalized nanodiamond 440*b* is not bound to an analyte, and can move freely through the subsurface vasculature 430. As a result, a proximity between the second individual functionalized nanodiamond 440*b* and individual functionalized magnetic particles is variable, and likely to be higher than the certain low range of distances related to the size of individual instances of the analyte.

The wrist-mounted device 400 could be configured to determine that an individual functionalized nanodiamond is proximate to at least one functionalized magnetic particle based on the detected one or more properties of the emitted light 452 from color centers of the individual functionalized nanodiamond. Additionally or alternatively, the wrist-mounted device 400 could be configured to convey information about the one or more properties of the emitted light 452 to another system, and the other system could be configured to determine that an individual functionalized nanodiamond 440 is proximate to at least one functionalized magnetic particle based on the conveyed information. For example, a rate at which the occupancy of spin or other quantum states of the color centers of the individual functionalized nanodiamond changes from a polarized state to an equilibrium state could be determined based on one or more detected amplitudes of the emitted light 452 corresponding to color centers of the individual functionalized nanodiamond. The determined rate could then be related to a proximity between the individual functionalized nanodiamond and one or more functionalized magnetic particles. Other detected properties of the emitted light 452 and/or methods could be used to determine that an individual functionalized nanodiamond is proximate to at least one functionalized magnetic particle.

The wrist-mounted device 400 could be configured to determine that an individual functionalized nanodiamond and at least one functionalized magnetic particle are bound to the analyte 490 based on a determination that the individual functionalized nanodiamond is proximate to the at least one functionalized magnetic particle. Additionally or alternatively, the wrist-mounted device 400 could be configured to convey information about the determination that the individual functionalized nanodiamond is proximate to the at least one functionalized magnetic particle to another system, and the other system could be configured to determine that the individual functionalized nanodiamond and the at least one functionalized magnetic particle. For example, the determination that the individual nanodiamond was less than a certain distance from the at least one functionalized magnetic particle could be used to determine that individual functionalized nanodiamond and at least one functionalized magnetic particle are bound to an instance of the analyte 490. This determination could be based on additional information; for example, it could be determined that the individual functionalized nanodiamond and at least one functionalized magnetic particle are bound to an instance of the analyte 490 if the proximity between the individual functionalized nanodiamond and the at least one functionalized magnetic particle was below a certain distance for a certain period of time. Other additional and/or alternative methods could be implemented by the wrist-mounted device 400.

The wrist-mounted device 400 could additionally include an electromagnetic field emitter (not shown). The electromagnetic field emitter could be configured to generate a variety of electrical, magnetic, and/or electromagnetic fields in the subsurface vasculature 430 to enable a variety of methods of detecting and/or determining properties of the subsurface vasculature 430, the functionalized nanodiamonds 440, the functionalized magnetic particles 480, and/or the analyte 490. In some examples, the electromagnetic field emitter could be configured to emit microwave radiation having a specified frequency. In some examples, the electromagnetic field emitter could be configured to emit an oscillating magnetic field such that the functionalized magnetic particles 480 are heated by energy from the oscillating magnetic field. In some examples, the electromagnetic field emitter could be configured to emit a DC magnetic field. In some examples, the electromagnetic field emitter could be configured to emit electromagnetic pulses configured to affect and/or control a direction, precession frequency, and/or some other property of a spin or other quantum state of one or more color centers contained in the functionalized nanodiamonds.

The elements of the wrist-mounted device 400 (e.g., light sensor 450, light emitter 460, electromagnetic field emitter) could additionally or alternatively be operated to enable a variety of methods for detecting and/or determining properties of the subsurface vasculature 430, the functionalized nanodiamonds 440, the functionalized magnetic particles 480, and/or the analyte 490. The methods implemented could be similar to those described herein. Other methods of detection and/or determination are anticipated.

FIG. 4 illustrates paths of the transmitted illumination 462 transmitted by the light source 460 and the emitted light 452 detected by the light sensor 450 that do not overlap. However, in some instances, the light source 460 and the light sensor 450 may be angled towards each other so that they are illuminating and sensing from essentially the same area of subsurface vasculature. Other configurations of light sources, light sensors, light paths, electromagnetic field generators, directed energy fields, and other elements are anticipated. Further, it is anticipated that more than one light source, field generator, or light sensor may be included to enable the embodiments and methods disclosed herein.

Method 300 could be expanded in a number of ways to enable to detection and/or determination of an environment, functionalized nanodiamonds, functionalized magnetic particles, and/or an analyte that the functionalized nanodiamonds and functionalized magnetic particles are configured to selectively interact with. In general, expansion of the method 300 includes optical detection of one or more properties of color centers in an individual functionalized nanodiamond that are related to proximity to at least one functionalized magnetic particle. The detected one or more properties could be used to determine one or more properties (e.g., a distance, a number of proximate functionalized magnetic particles) of the proximity between the individual functionalized nanodiamond and the at least one functionalized magnetic particle. The determined one or more properties of the proximity could then be used to determine information about the analyte; for example, that the individual functionalized nanodiamond is bound to an instance of the analyte, a concentration of the analyte in the environment, or some other information about the analyte, the environment, and/or the functionalized particles.

In general, method 300 and expansions thereof include steps that include illuminating color centers in functionalized nanodiamonds. Illumination of color centers in functionalized nanodiamonds (where the color centers and functionalized nanodiamonds are configured as described herein) generally has at least two effects on the color centers. First, illumination can cause the color centers to emit light having one or more properties (e.g., an amplitude, a frequency, a latency) related to the occupancy of spin or other quantum states of the color centers. For example, occupancy of a first set of states could result in a first level of fluorescence amplitude, and occupancy of a second set of states could result in a second level of fluorescence, such that a detected level of fluorescence amplitude could be used to determine to what degree the first and second states are occupied. Second, illumination can cause the occupancy of spin or other quantum states of the color centers to change. In some examples, this could occur through the same mechanism used to cause the emission of light by the color centers in response to illumination. In some examples, this could result in only a single state of the spin or other quantum states of the color centers being occupied after being exposed to illumination having specified properties for a specified period of time; that is, illumination of the color centers could polarize the occupancy of the spin or other quantum states of the color centers.

Figure 5:
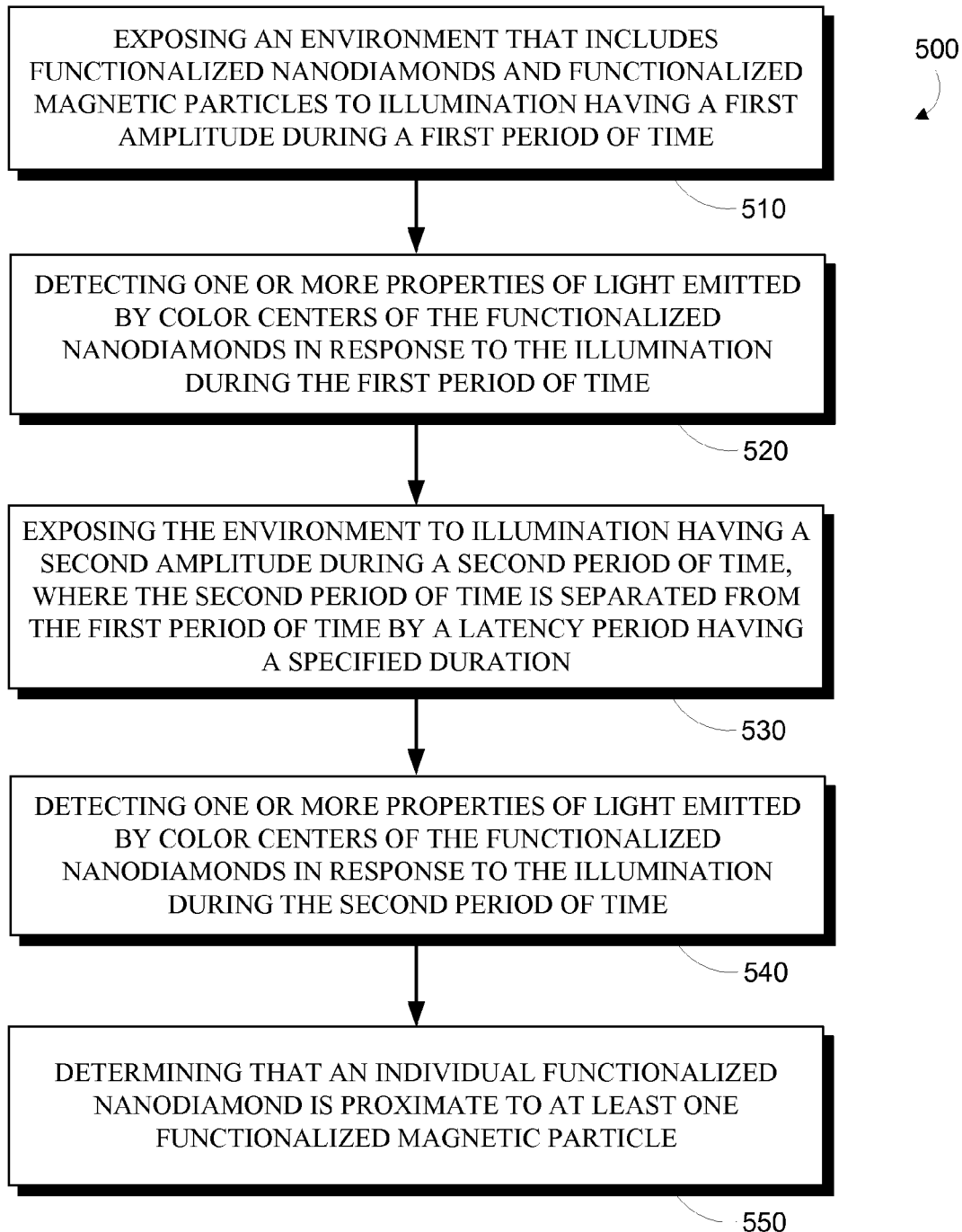
FIG. 5 is a flowchart of an example method.

FIG. 5 is a flowchart of a method 500 for determining that an individual functionalized nanodiamond in an environment is proximate to at least one functionalized magnetic particle in the environment. Each functionalized nanodiamond and functionalized magnetic particle is configured to selectively interact with an analyte (e.g., by binding to one or more proteins, ligands, or other elements of the analyte). Each functionalized nanodiamond contains at least one color center configured to emit light in response to illumination of the at least one color center. Further, one or more properties of light emitted by individual color centers in response to illumination is related to proximity between the individual color centers and the functionalized magnetic particles. In some examples, this includes the color centers having two or more spin or other quantum states, wherein the amount of light emitted by the color centers in response to illumination is related to the occupancy of the spin or other quantum states, and wherein an individual functionalized magnetic particle proximate to a color center is configured to emit a time-varying electromagnetic field such that the occupancy of the spin or other quantum states of the proximate color center is affected by the emitted time-varying electromagnetic field.

The method 500 includes, during a first period of time, exposing the environment that includes the functionalized nanodiamonds and the magnetic particles to illumination having a first amplitude 510 and detecting one or more properties of light emitted by the color centers of the functionalized nanodiamonds in response to the illumination 520. Exposing the environment to illumination 510 can include emitting illumination having a specified amplitude, phase, polarization, or other property. Detecting one or more properties of light emitted by the color centers 520 can include detecting the amplitude, wavelength, degree of polarization, orientation of polarization, location, or other properties of the emitted light. The first period of time could have a specified duration. For example, the first period of time could have a duration specified such that, when exposed to illumination having the first amplitude over a period of time equal to the specified duration, spin or other quantum states of color centers in functionalized nanodiamonds in the environment become substantially polarized (i.e., only a single state or restricted set of states of the spin or other quantum states of the color centers is occupied).

The method 500 includes, during a second period of time, exposing the environment that includes the functionalized nanodiamonds and the magnetic particles to illumination having a second amplitude 530 and detecting one or more properties of light emitted by the color centers of the functionalized nanodiamonds in response to the illumination 540. The second period of time could have a specified duration. The specified duration could be sufficiently long to allow the occupancy of spin or other quantum states of color centers in functionalized nanodiamonds in the environment to be determined and/or detected. The second period of time could directly follow the first period of time (i.e., a latency between the end of the first period and the beginning of the second period could be zero), or could follow the first period after a latency period having specified duration. In some examples, the duration of the latency period could be specified such that a difference in a detected property of the light emitted by the color centers during the first and second periods of time (i.e., the properties of the light detected in 520 and 540) that is related to the proximity between the individual color centers and the functionalized magnetic particles. For example, the duration of the latency period could be specified such that a difference in a rate of change of spin or other quantum states of the color centers of an individual functionalized nanodiamond could be detected, and such that the detected rate of change is detectably different between an individual functionalized nanodiamond that is proximate to at least one functionalized magnetic particle and an individual functionalized nanodiamond that is not proximate to at least one functionalized magnetic particle.

The method 500 includes determining that an individual functionalized nanodiamond is proximate to at least one magnetic particle 550 based on at least the specified duration of the latency period, the second amplitude, and a detected property of the light emitted by the color centers of the individual functionalized nanodiamond in response to the illumination during the second period of time. In some examples, this determination could include determining a rate at which the occupancy of spin or other quantum states of the color centers of the individual functionalized nanodiamond changes from a polarized state to an equilibrium state. This could be accomplished by comparing a first fluorescence intensity of the color centers that is determined during the first period of time (based, e.g., on the first amplitude of illumination and a detected amplitude of light emitted by the color centers) with a second fluorescence intensity that is determined during the second period of time. The presence of at least one functionalized magnetic particle, producing electromagnetic radiation sufficient to affect the occupancy of the spin or other quantum states of the color centers and thus to change the rate at which the occupancy of spin or other quantum states of the color centers changes over time. A first rate of change could be related to color centers contained in functionalized nanodiamonds that are not proximate to at least one functionalized magnetic particle, and the determining that an individual functionalized nanodiamond is proximate to at least one magnetic particle 550 could include determining that a rate of change corresponding to the individual functionalized nanodiamond was substantially different from the first rate of change.

In some examples, the method 500 could be performed a plurality of times, with individual instances of method 500 having respective first and second amplitudes, detected properties of light emitted from color centers, durations of first and second time periods, durations of latencies, or other properties. For example, the rate of change of occupancy of spin or other quantum states of the color centers in an individual functionalized nanodiamond could be a time-varying function, and the method 500 could be performed a plurality of times having a respective plurality of latencies such that the time varying function could be determined. The time varying function could then be used to determine that the individual functionalized nanodiamond was proximate to at least one functionalized magnetic particle, or to determine other information.

The method 500 could further include determining that an individual functionalized nanodiamond and at least one functionalized magnetic particle are bound to the analyte based on the determination that the individual functionalized nanodiamond is proximate to the at least one functionalized magnetic particle 550. For example, the determination that an individual nanodiamond was less than a certain distance from one or more magnetic particles could be used to determine that one or more instances of the analyte was proximate to the individual nanodiamond and at least one magnetic particle 550. This determination could be based on additional information; for example, it could be determined that one or more instances of the analyte was proximate to an individual nanodiamond and at least one magnetic particle if the proximity between the individual nanodiamond and the at least one magnetic particle was below a certain distance for a certain period of time. Other additional and/or alternative elements of method 500 are anticipated.

In some examples, determining information about the analyte, the environment, and/or the functionalized particles could include exposing the environment to microwave radiation. This exposure could enable the determination, based on one or more properties of light emitted by color centers contained in an individual functionalized nanodiamond in the environment in response to illumination, of one or more properties of the environment proximate to the individual functionalized nanodiamond (e.g., a DC magnetic field, a temperature, a time-varying electromagnetic field).

For example, exposing the environment to microwave radiation having a specified frequency could enable the determination that a difference in energy levels between two or more allowed spin or other quantum states of the color centers corresponded to an energy level corresponding to the specified frequency. That is, a rate of change of occupancy between the two or more allowed spin or other quantum states could be detected optically (e.g., by illuminating the environment and detecting one or more properties of light emitted by the color centers in response to the illumination). If the specified frequency does not correspond to two or more allowed energy states, exposure to the microwave radiation can have no effect on the rate of change of occupancy of states of the color centers. The environment could be exposed to microwave radiation having a variety of frequencies, enabling the determination of a magnetic resonance spectrum of the color centers that is related to the energy difference between allowed spin or other quantum mechanical states of the color centers. Other applications and methods are anticipated.

Figure 6:
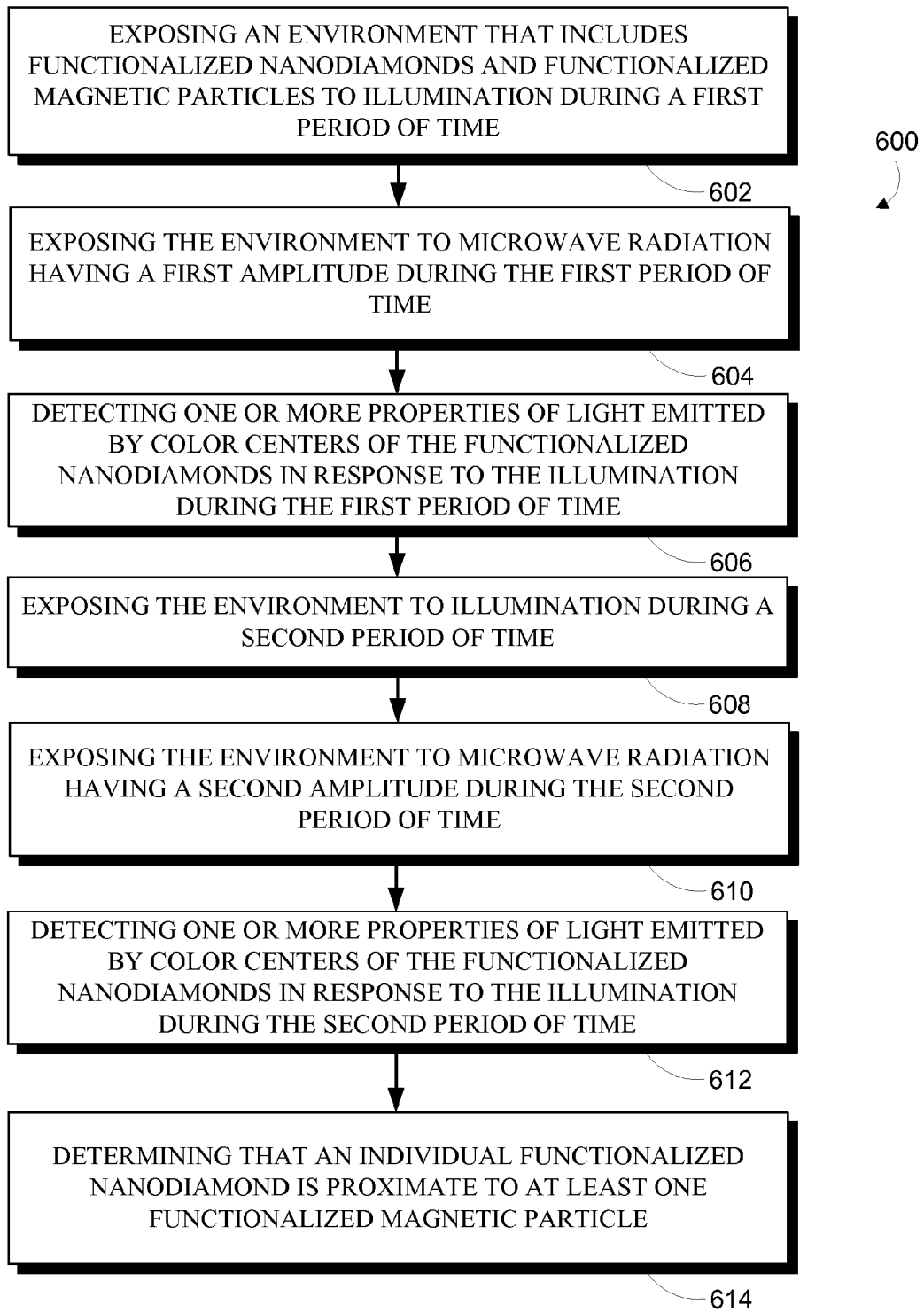
FIG. 6 is a flowchart of an example method.

FIG. 6 is a flowchart of a method 600 for determining that an individual functionalized nanodiamond in an environment is proximate to at least one functionalized magnetic particle in the environment. Each functionalized nanodiamond and functionalized magnetic particle is configured to selectively interact with an analyte (e.g., by binding to one or more proteins, ligands, or other elements of the analyte). Each functionalized nanodiamond contains at least one color center configured to emit light in response to illumination of the at least one color center. Further, one or more properties of light emitted by individual color centers in response to illumination is related to proximity between the individual color centers and the functionalized magnetic particles and to one or more properties of microwave radiation in the environment. In some examples, this includes the color centers having two or more spin or other quantum states having a difference in energy, wherein the magnitude of a light emitted by the color centers in response to illumination is related to the occupancy of the spin or other quantum states, wherein an individual functionalized magnetic particle proximate to a color center can cause a change in the difference in energy, and wherein the presence of microwave energy in the environment having a frequency corresponding to the difference in energy can affect the occupancy of the spin or other quantum states of the proximate color.

The method 600 includes, during a first period of time, exposing the environment that includes the functionalized nanodiamonds and the magnetic particles to illumination 602, exposing the environment to microwave radiation having a first amplitude 604 and detecting one or more properties of light emitted by the color centers of the functionalized nanodiamonds in response to the illumination 606. Exposing the environment to illumination 602 can include emitting illumination having a specified amplitude, phase, polarization, or other property. Exposing the environment to microwave radiation 604 can include emitting microwave radiation having the first amplitude and having a specified phase, frequency, polarization, or other property. In some examples, the frequency of the microwave radiation could be specified to correspond to an energy level difference between spin or other quantum states of a color center. For example, the color center could be a negatively-charged nitrogen vacancy center (NV− center) in diamond, and the specified frequency could be approximately 2.869 gigahertz corresponding to an energy level difference between first and second spin states of the NV− center at room temperature and in an environment having a magnetic field having substantially no magnitude in a direction parallel to the z-direction of the NV− center. Detecting one or more properties of light emitted by the color centers 606 can include detecting the amplitude, wavelength, degree of polarization, orientation of polarization, location, or other properties of the emitted light. The first period of time could have a specified duration. For example, the first period of time could have a duration specified such that, when exposed to the illumination and the microwave radiation over a period of time equal to the specified duration, the occupancy of spin or other quantum states of color centers in functionalized nanodiamonds in the environment reach a first equilibrium level related to the first amplitude of the microwave radiation. Further, detecting one or more properties of light emitted by the color centers 606 can enable the determination of the first equilibrium level of occupancy of the spin or other quantum states of the color centers.

The method 600 includes, during a second period of time, exposing the environment that includes the functionalized nanodiamonds and the magnetic particles to illumination 608, exposing the environment to microwave radiation having a second amplitude 610 and detecting one or more properties of light emitted by the color centers of the functionalized nanodiamonds in response to the illumination 612. The second period of time could have a specified duration. For example, the second period of time could have a duration specified such that, when exposed to the illumination and the microwave radiation over a period of time equal to the specified duration, the occupancy of spin or other quantum states of color centers in functionalized nanodiamonds in the environment reach a second equilibrium level related to the second amplitude of the microwave radiation. Further, detecting one or more properties of light emitted by the color centers 612 can enable the determination of the second equilibrium level of occupancy of the spin or other quantum states of the color centers.

The method 600 includes determining that an individual functionalized nanodiamond is proximate to at least one magnetic particle 614 based on at least the first amplitude of the microwave radiation, the second amplitude of the microwave radiation, and the detected properties of the light emitted by the color centers of the individual functionalized nanodiamond in response to the illumination during the first and second periods of time, respectively. In some examples, the microwave radiation emitted during the first and second periods could have a specified frequency, and determining that an individual functionalized nanodiamond is proximate to at least one magnetic particle 614 could include determining that the first equilibrium state and the second equilibrium state are substantially the same. The specified frequency could correspond to a difference in energy between states of a color center that is not proximate to at least one functionalized magnetic particle. Thus, being exposed to the microwave radiation having the specified frequency could cause a change in occupancy of the states of the color center that is not proximate to at least one functionalized magnetic particle. In contrast, the difference in energy between states of the color center could change when the color center was proximate to at least one functionalized magnetic particle (e.g., through Zeeman splitting and shifting of the spin or other quantum states or through other mechanisms). Thus, being exposed to the microwave radiation having the specified frequency could cause less change in occupancy of the states of the color center when the color center is proximate to at least one functionalized magnetic particle. Detected changes in occupancy of the states of the color center could be used to determine that the individual functionalized nanodiamond is proximate to at least one magnetic particle 614.

Determining that the first equilibrium state and the second equilibrium state are substantially the same could be accomplished by comparing a first fluorescence intensity of the color centers that is determined during the first period of time (based, e.g., on detected amplitude of light emitted by the color centers during the first period and an amplitude of the illumination during the first period) with a second fluorescence intensity that is determined during the second period of time. The first fluorescence intensity and second fluorescence intensity being substantially the same could be used to determine that the first equilibrium state and the second equilibrium state are substantially the same, and thus to determine that the individual functionalized nanodiamond is proximate to at least one magnetic particle 614.

The method 600 could further include determining that an individual functionalized nanodiamond and at least one functionalized magnetic particle are bound to the analyte based on the determination that the individual functionalized nanodiamond is proximate to the at least one functionalized magnetic particle 614. For example, the determination that an individual nanodiamond was less than a certain distance from one or more magnetic particles could be used to determine that one or more instances of the analyte was proximate to the individual nanodiamond and at least one magnetic particle 614. This determination could be based on additional information; for example, it could be determined that one or more instances of the analyte was proximate to an individual nanodiamond and at least one magnetic particle if the proximity between the individual nanodiamond and the at least one magnetic particle was below a certain distance for a certain period of time. Other additional and/or alternative elements of method 600 are anticipated.

Figure 7:
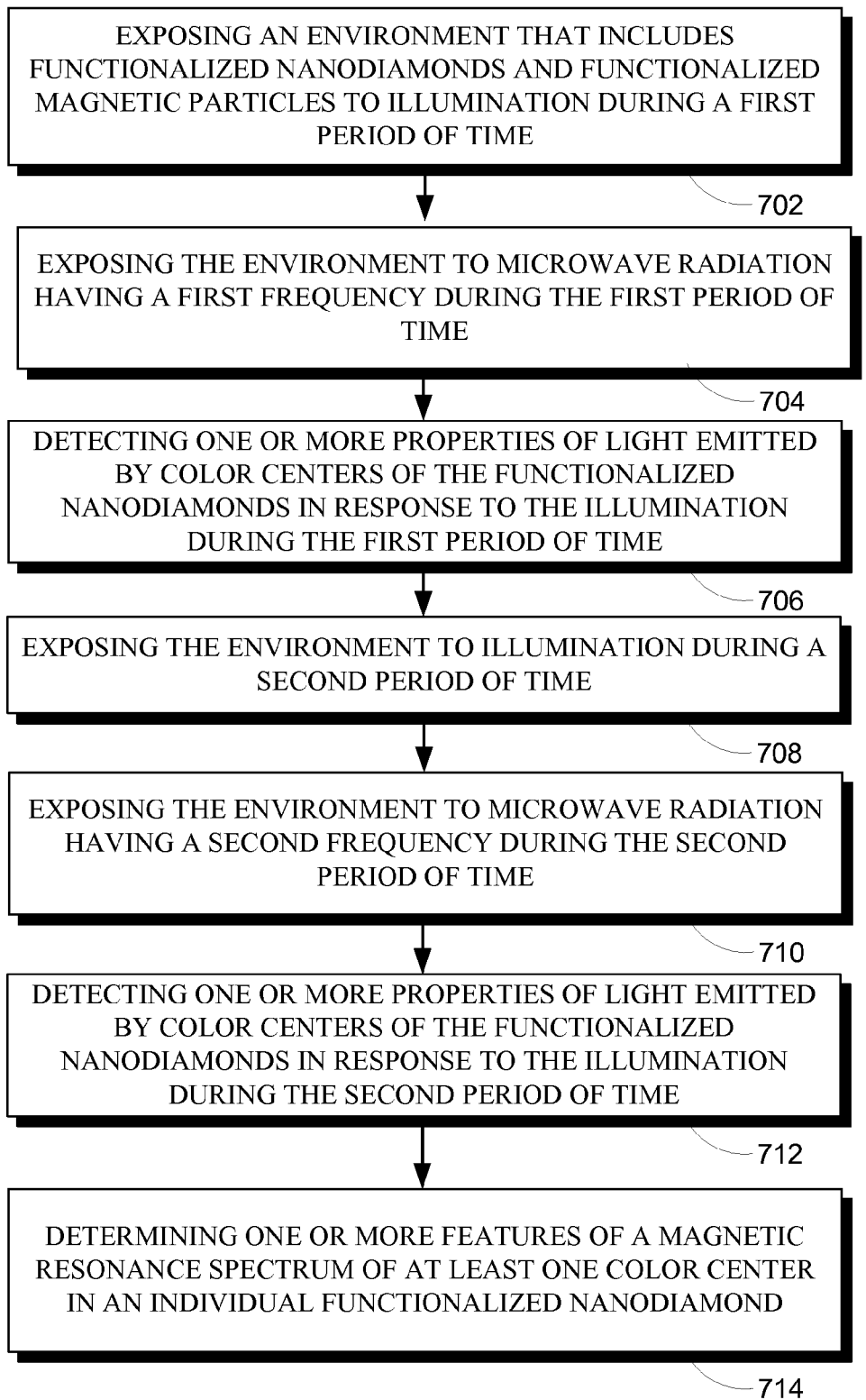
FIG. 7 is a flowchart of an example method.

FIG. 7 is a flowchart of a method 700 for determining features of a magnetic resonance spectrum of color centers contained in an individual functionalized nanodiamond in an environment that additionally contains functionalized magnetic particles. Each functionalized nanodiamond and functionalized magnetic particle is configured to selectively interact with an analyte (e.g., by binding to one or more proteins, ligands, or other elements of the analyte). Each functionalized nanodiamond contains at least one color center configured to emit light in response to illumination of the at least one color center. Further, the at least one color center has a magnetic resonance spectrum that has at least one feature (e.g., an absorbance peak, an absorbance peak width, a number of absorbance peaks). Further, one or more properties of the magnetic resonance spectrum are related to related to one or more properties of light emitted by the at least one color center in response to illumination of the at least one color center. In some examples, this includes the color centers having a fluorescence intensity that is related to a feature of the magnetic resonance spectrum and to a frequency or other property of microwave radiation to which the color centers are exposed.

The method 700 includes, during a first period of time, exposing the environment that includes the functionalized nanodiamonds and the magnetic particles to illumination 702, exposing the environment to microwave radiation having a first frequency 704 and detecting a first amplitude of light emitted by the color centers of the functionalized nanodiamonds in response to the illumination 706. Exposing the environment to illumination 702 can include emitting illumination having a specified amplitude, phase, polarization, or other property. Exposing the environment to microwave radiation 704 can include emitting microwave radiation having the first frequency and having a specified phase, amplitude, polarization, or other property. The first period of time could have a specified duration. For example, the first period of time could have a duration specified such that, when exposed to the illumination and the microwave radiation over a period of time equal to the specified duration, the occupancy of spin or other quantum states of color centers in functionalized nanodiamonds in the environment reach a first equilibrium level related to the first frequency of the microwave radiation. Further, detecting the first amplitude of light emitted by the color centers 706 can enable the determination of the first equilibrium level of occupancy of the spin or other quantum states of the color centers.

The method 700 includes, during a second period of time, exposing the environment that includes the functionalized nanodiamonds and the magnetic particles to illumination 708, exposing the environment to microwave radiation having a second frequency 710 and detecting a second amplitude of light emitted by the color centers of the functionalized nanodiamonds in response to the illumination 712. The second period of time could have a specified duration. For example, the second period of time could have a duration specified such that, when exposed to the illumination and the microwave radiation over a period of time equal to the specified duration, the occupancy of spin or other quantum states of color centers in functionalized nanodiamonds in the environment reach a second equilibrium level related to the second frequency of the microwave radiation. Further, detecting the second amplitude of light emitted by the color centers 712 can enable the determination of the second equilibrium level of occupancy of the spin or other quantum states of the color centers.

The method 700 includes determining one or more features of a magnetic resonance spectrum at least one color center in an individual functionalized nanodiamond 714 using at least the first and second specified frequencies of the microwave radiation and the first and second detected amplitudes of the light emitted by the color centers in response to illumination during the first and second periods, respectively. The one or more features could be the location, width, or other properties of an absorbance peak of the magnetic resonance spectrum of the color centers. In an example, the first specified frequency could be a center frequency of an absorbance peak, and the second specified frequency could be a different frequency that is at another location on the absorbance peak. The one or more features could be a degree of broadening of the absorbance peak, and could be determined based on the first detected amplitude that corresponds to a value of the magnetic resonance spectrum at the first frequency (i.e., the center frequency of the absorption peak) and the second detected amplitude that corresponds to a value of the magnetic resonance spectrum at the second frequency. The degree of broadening of the absorbance peak could be related to a ratio, a difference, or some other function of the first and second values of the magnetic resonance spectrum at the respective first and second frequencies.

In some examples, a plurality of values of the magnetic resonance spectrum could be determined by, during a plurality of time periods, illuminating the environment, exposing the environment to microwave radiation having respective specified frequencies, and detecting respective properties of light emitted by color centers of the functionalized nanodiamonds. The magnetic resonance spectrum could be determined at a specified resolution (related to differences between the plurality of specified frequencies of the microwave radiation). Additionally or alternatively, the magnetic resonance spectrum could be determined at different resolutions for different ranges of frequencies. For example, the magnetic resonance spectrum could be determined at a higher resolution for a range of frequencies that are known to contain a narrow absorbance peak.

In some examples, multiple features of the magnetic resonance spectrum could be determined. For examples, both a center frequency and a width of an absorbance peak could be determined by determining two or more values of the magnetic resonance spectrum at two or more specified frequencies. Further, features of the magnetic resonance spectrum could be related to properties of the environment, the functionalized nanodiamonds, the functionalized magnetic particles, an analyte, or some other variable (e.g., temperature, a magnitude or direction of an electrical field, a magnitude or direction of a magnetic field, a temperature, a mechanical strain). For example, the location of an absorbance peak could be related to a temperature of a functionalized nanodiamond and a width of an absorbance peak could be related to a magnitude of a DC magnetic field. In some examples, a single absorbance peak could have multiple features related to respective multiple properties of the environment, the functionalized nanodiamonds, the functionalized magnetic particles, and/or an analyte.

The method 700 could further include determining that an individual functionalized nanodiamond and at least one functionalized magnetic particle are proximate using the determined one or more properties of the magnetic resonance spectrum. In some examples, the determined one or more features of the magnetic resonance spectrum could include a degree of widening of an absorbance peak of the magnetic resonance spectrum. The degree of widening of the absorbance peak could be related to a DC magnetic field in the environment of the functionalized nanodiamonds; the DC magnetic field could in turn be generated by at least one functionalized magnetic particle proximate to the functionalized nanodiamond. The method 700 could include determining that an individual functionalized nanodiamond is proximate to at least one functionalized magnetic particle based on a determined degree of widening of an absorbance peak of the magnetic resonance spectrum.

The method 700 could further include determining that an individual functionalized nanodiamond and at least one functionalized magnetic particle are bound to an analyte based on the determination that the individual functionalized nanodiamond is proximate to the at least one functionalized magnetic particle. For example, the determination that an individual nanodiamond was less than a certain distance from one or more magnetic particles could be used to determine that one or more instances of the analyte was proximate to the individual nanodiamond and at least one magnetic particle. This determination could be based on additional information; for example, it could be determined that one or more instances of the analyte was proximate to an individual nanodiamond and at least one magnetic particle if the proximity between the individual nanodiamond and the at least one magnetic particle was below a certain distance for a certain period of time. Other additional and/or alternative elements of method 700 are anticipated.

Proximity between an individual functionalized nanodiamond and at least one functionalized magnetic particle could be determined through a variety of additional methods. In general, determining that an individual functionalized nanodiamond and at least one functionalized magnetic particle are proximate includes optically detecting (i.e., illuminating color centers contained in the functionalized nanodiamond and detecting one or more properties of light emitted by the color centers in response to the illumination) one or more properties of the color centers that are related to effects of functionalized magnetic particles proximate to the individual functionalized nanodiamond. For example, a DC magnetic field, a time-varying magnetic field, or some other effect of the functionalized magnetic particle on the environment proximate to the functionalized magnetic particle could cause changes in the optical properties of the color centers. Additionally, detection of these properties could be enabled by emission of electromagnetic radiation (e.g., microwave radiation) or other energies having specified properties (e.g., amplitude, frequency, timing). For example, the functionalized magnetic particles could be exposed to an oscillating electromagnetic field (e.g., a radio wave having a frequency between 1 kilohertz and 1000 megahertz) such that an individual functionalized magnetic particle could cause heating of a region proximate to the individual functionalized magnetic particle.

Figure 8:
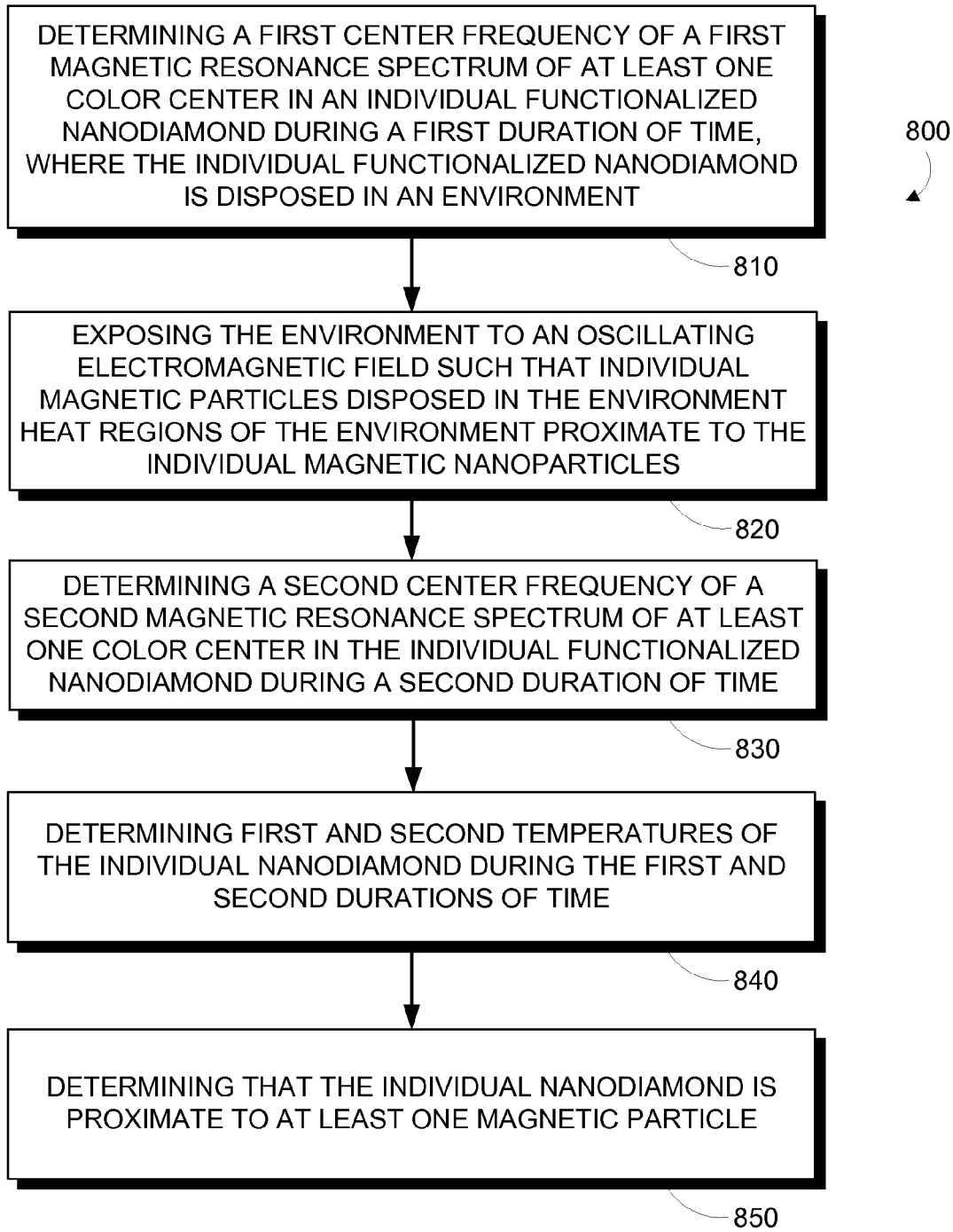
FIG. 8 is a flowchart of an example method.

FIG. 8 is a flowchart of a method 800 for determining that an individual functionalized nanodiamond in an environment is proximate to at least one functionalized magnetic particle in the environment. Each functionalized nanodiamond and functionalized magnetic particle is configured to selectively interact with an analyte (e.g., by binding to one or more proteins, ligands, or other elements of the analyte). Each functionalized nanodiamond contains at least one color center configured to emit light in response to illumination of the at least one color center. Further, the at least one color center has a magnetic resonance spectrum that has at least one absorbance peak that has a center frequency related to the temperature of the color center. Further, one or more properties of the magnetic resonance spectrum are related to related to one or more properties of light emitted by the at least one color center in response to illumination of the at least one color center. In some examples, this includes the color centers having a fluorescence intensity that is related to a feature of the magnetic resonance spectrum and to a frequency or other property of microwave radiation to which the color centers are exposed.

The method 800 includes, during a first duration of time, determining a first center frequency of the magnetic resonance spectrum of at least one color center in an individual functionalized nanodiamond 810. Determining a first center frequency of the magnetic resonance spectrum of at least one color center 810 can include one or more of the methods described herein and/or one or more methods familiar to one of ordinary skill in the art to determine and/or detect features of a magnetic resonance spectrum of a color center in diamond. For example, two or more fluorescence intensities of the color center could be detected when the color center is exposed to microwave radiation having two or more respective frequencies and the two or more fluorescence intensities could be used to determine one or more properties of the magnetic resonance spectrum of the color center.

The method 800 includes exposing the environment to an oscillating electromagnetic field such that individual functionalized magnetic particles in the environment heat regions of the environment proximate to the individual functionalized magnetic particles 820. Exposing the environment to an oscillating electromagnetic field 820 could include emitting an oscillating electromagnetic field having a frequency between 1 kilohertz and 1000 megahertz. Exposing the environment to an oscillating electromagnetic field 820 could include emitting an oscillating electromagnetic field having a specified frequency related to one or more properties of the functionalized magnetic particles. For example, the specified frequency could be specified such that only functionalized magnetic particles having a size within a specified range could heat proximate regions of the environment. Exposing the environment to an oscillating electromagnetic field 820 could include emitting an oscillating electromagnetic field using a coil, antenna, or other emitter that is also used to emit microwaves or other electromagnetic radiation to determine a center frequency or other information about a magnetic resonance spectrum of a color center in functionalized nanodiamonds in the environment.

The method 800 includes, during a second duration of time, determining a second center frequency of the magnetic resonance spectrum of the at least one color center in the individual functionalized nanodiamond 830. Determining a second center frequency of the magnetic resonance spectrum of at least one color center 830 can include one or more of the methods described herein and/or one or more methods familiar to one of ordinary skill in the art to determine and/or detect features of a magnetic resonance spectrum of a color center in diamond. For example, two or more fluorescence intensities of the color center could be detected when the color center is exposed to microwave radiation having two or more respective frequencies and the two or more fluorescence intensities could be used to determine one or more properties of the magnetic resonance spectrum of the color center.

The method 800 includes determining first and second temperatures of the individual functionalized nanodiamond corresponding to the respective first and second durations of time 840. This could include using a look-up table, equation, model, or other program or function to relate the determined first and second center frequencies to respective first and second temperatures. For example, the color centers could be NV− centers, and the determined center frequency of the magnetic spectrum could increase by approximately 75 kilohertz in response to every degree Celsius increase in the temperature of the color center.

The method 800 includes determining that an individual functionalized nanodiamond is proximate to at least one magnetic particle 850 based on the determined first and second temperatures and one or more properties of the oscillating electromagnetic field. Determining that an individual functionalized nanodiamond is proximate to at least one magnetic particle 850 could include determining that a difference between the first and second temperatures was greater than a specified threshold. The specified threshold could be based on a specific heat, a thermal conductivity, and/or some other property of the environment, the individual functionalized nanodiamonds, the functionalized magnetic particles, the analyte, or some other element in the environment. Other methods of determining that an individual functionalized nanodiamond is proximate to at least one magnetic particle 850 based on the determined first and second temperatures and one or more properties of the oscillating electromagnetic field are anticipated.

The method 800 could further include determining that an individual functionalized nanodiamond and at least one functionalized magnetic particle are bound to the analyte based on the determination that the individual functionalized nanodiamond is proximate to the at least one functionalized magnetic particle 850. For example, the determination that an individual nanodiamond was less than a certain distance from one or more magnetic particles could be used to determine that one or more instances of the analyte was proximate to the individual nanodiamond and at least one magnetic particle 850. This determination could be based on additional information; for example, it could be determined that one or more instances of the analyte was proximate to an individual nanodiamond and at least one magnetic particle if the proximity between the individual nanodiamond and the at least one magnetic particle was below a certain distance for a certain period of time. Other additional and/or alternative elements of method 800 are anticipated.

The method 800 could additionally or alternatively include other functionalized particles configured to heat regions of the environment proximate to the other functionalized particles. The other functionalized particles could be any particles that selectively interact with the analyte and that can receive an energy to which the environment is exposed and transduce the received energy into an increase into heat in regions of the environment proximate to the other functionalized particles. In some examples, the other functionalized particles could be configured to receive an acoustical energy or some other pressure wave in the environment. In some examples, the other functionalized particles could be configured to receive visible light, infrared light, ultraviolet light, or some other electromagnetic energy.

In some examples, the environment described in relation to the methods 300, 500, 600, 700, 800 above could be a portion of vasculature in a human body. For example, the environment could be a lumen of subsurface vasculature of a wearer of a device that is configured to implement and execute elements of the method(s) 300, 500, 600, 700, 800 (e.g., device 400, or one of the devices described below (e.g., 900, 1000, 1100, 1200, 1300, 1400)). In some examples, the analyte in the environment could be a cell. For example, the environment could be a tissue of a human, and the analyte could be a cancer cell. The engineered particles could be functionalized to selectively interact with the cancer cell by being attached to a bioreceptor that is selectively receptive to one or more elements of the cancer cell, e.g., a membrane-spanning protein. Other examples of environments, analytes, configurations of functionalized nanodiamonds containing color centers and/or functionalized magnetic particles, and other elements are anticipated.

The example embodiments described herein generally include a single variety of color-center-containing functionalized nanodiamond and a single variety of functionalized magnetic particle used to image and/or determine one or more properties of an analyte in an environment. However, more than one type of functionalized nanodiamond and/or functionalized magnetic particle could be used to determine one or more properties of more than one respective analyte in an environment. Additionally or alternatively, one or more of the respective analytes could be components of an analyte of interest, e.g., the analyte of interest could be a cancer cell and respective analytes could be unique markers on the surface of the cancer cell. One or more properties of the analyte of interest could be determined based on information about the respective analytes determined from information about respective functionalized nanodiamonds and/or respective functionalized magnetic particles.

IV. Example Devices

Figure 9:
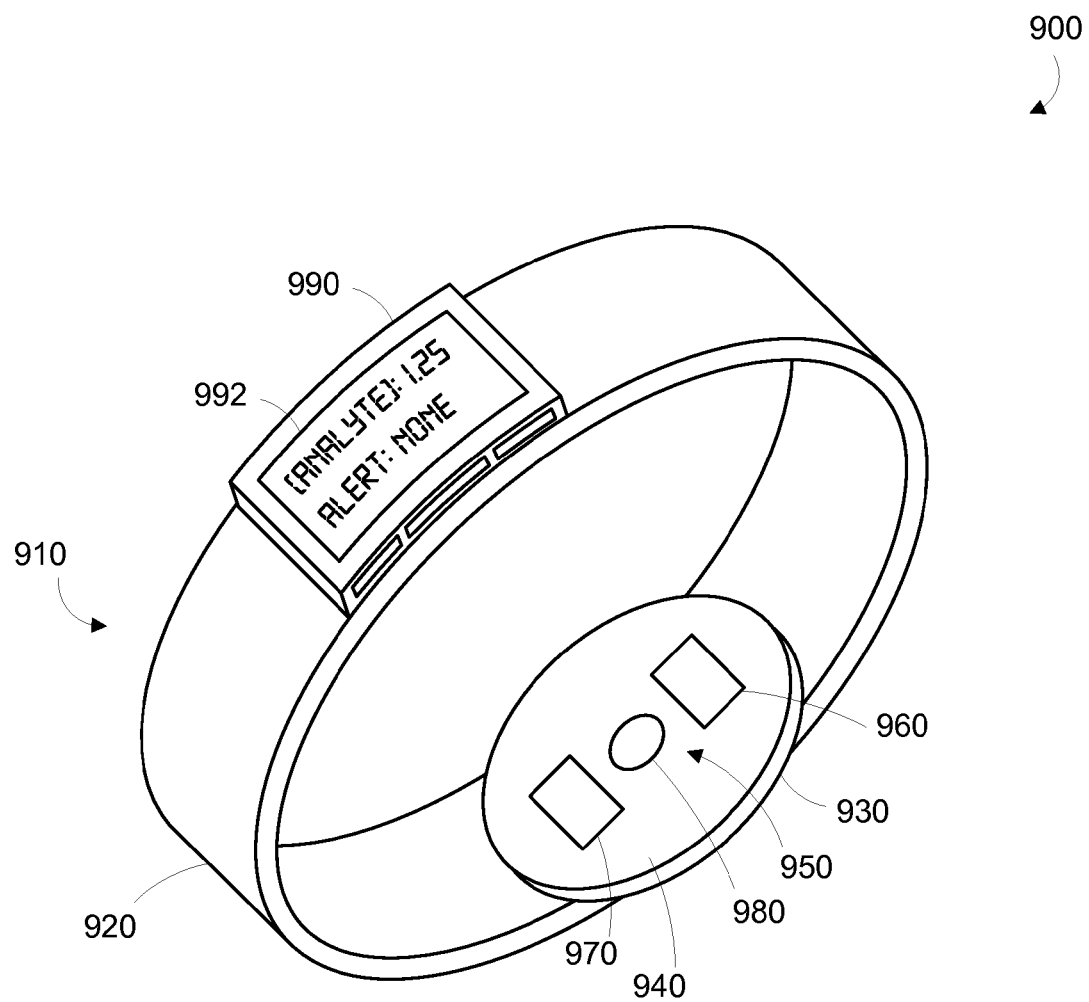
FIG. 9 is a perspective view of an example wearable device.

A wearable device 900 (illustrated in FIG. 9) can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 910, such as a belt, wristband, ankle band, etc. can be provided to mount the device at, on or in proximity to the body surface. The mount 910 may prevent the wearable device from moving relative to the body to reduce measurement error and noise. In one example, shown in FIG. 9, the mount 910, may take the form of a strap or band 920 that can be worn around a part of the body. Further, the mount 910 may be an adhesive substrate for adhering the wearable device 900 to the body of a wearer.

A measurement platform 930 is disposed on the mount 910 such that it can be positioned on the body where subsurface vasculature is easily observable. An inner face 940 of the measurement platform is intended to be mounted facing to the body surface. The measurement platform 930 may house a data collection system 950, which may include at least one detector 960 for detecting at least one physiological parameter, which could include any parameters that may relate to the health of the person wearing the wearable device. For example, the detector 960 could be configured to measure blood pressure, pulse rate, respiration rate, skin temperature, etc. In a non-exhaustive list, detector 960 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 950 may be miniaturized so that the wearable device may be worn on the body without significantly interfering with the wearer's usual activities.

At least one of the detectors 960 is a light sensor configured to detect one or more properties of light emitted by color centers in functionalized nanodiamonds in blood circulating in subsurface vasculature proximate to the wearable device 900. The light sensor could be a photodiode, a photomultiplier, a CCD, a photocell, a photoresistive element, a camera, or any other sensor or sensors configured to detect one or more properties of light emitted by color centers of the functionalized nanodiamonds.

The color centers of the functionalized nanodiamonds emit light in response to illumination of the color centers, and the detected one or more properties of the emitted light are related to the proximity between the color centers and functionalized magnetic particles in the blood circulating in the subsurface vasculature. The light sensor could include a filter that is configured to substantially block light emitted by a light source 970 of the data collection system 950.

The data collection system 950 further includes a light source 970 for transmitting illumination that can penetrate the wearer's skin into the portion of subsurface vasculature, for example, into a lumen of the subsurface vasculature. The transmitted illumination can be any kind of illumination that is benign to the wearer and that results at least in absorption of light energy by color centers contained in functionalized nanodiamonds proximate to the light source 970. The wavelength of the transmitted illumination could be specified to penetrate biological tissues of a wearer; for example, the transmitted illumination could have a wavelength within a near-infrared (NIR) transparency window of biological tissue. The wavelength of the transmitted illumination could be specified to be a wavelength that causes fluorescence and/or emission of light by the color centers. In some examples, the color centers could be negatively-charged nitrogen vacancy centers, and the wavelength of the transmitted illumination could be between approximately 500 and 650 nanometers. The light source 970 could be configured to produce additional illumination that results in emission of light by other chemicals, imaging agents, biological elements, or other analytes proximate to the light source 970.

An electromagnetic field emitter 980 may also be included in the data collection system 950. In such embodiments, the electromagnetic field emitter 980 may be configured to emit a variety of electrical, magnetic, and/or electromagnetic fields into the portion of subsurface vasculature to enable a variety of methods of detecting and/or determining properties of the portion of subsurface vasculature, functionalized nanodiamonds, functionalized magnetic particles, and/or analytes proximate to the device 900. In some examples, the electromagnetic field emitter 980 could be configured to emit microwave radiation having a specified frequency. In some examples, the electromagnetic field emitter 980 could be configured to emit electromagnetic radiation configured to affect and/or control the occupancy of one or more spin or other quantum states of one or more color centers contained in the functionalized nanodiamonds. In some examples, the electromagnetic field emitter 980 could be configured to emit an oscillating magnetic field such that the functionalized magnetic particles are heated by energy from the oscillating magnetic field. In some examples, the electromagnetic field emitter 980 could be configured to emit a DC magnetic field. In some examples, the electromagnetic field emitter 980 could be configured to emit electromagnetic pulses configured to affect and/or control a direction, precession frequency, and/or some other property of a spin or other quantum state of one or more color centers contained in the functionalized nanodiamonds.

The electromagnetic field emitter 980 could employ more than one of the methods disclosed herein or elsewhere to control, induce, modulate, or otherwise affect one or more properties of functionalized nanodiamonds, functionalized magnetic particles, analytes, or other element in an environment of interest. In some examples, acoustic waves could be emitted into the environment to selectively heat functionalized acoustic absorbers; the temperature of functionalized nanodiamonds in the environment could be detected and used to determine a proximity between the functionalized nanodiamonds and the functionalized acoustic absorbers. In some examples, the electromagnetic field emitter 980 could generate continuous and/or pulsed microwave energy to manipulate a direction of spins of color centers in functionalized nanodiamonds in the environment. For example, the continuous and/or pulsed microwave energy could be used to manipulate spins of color centers according to techniques used in nuclear magnetic resonance spectroscopy, nuclear magnetic resonance imaging, or other magnetic resonance techniques. Other operations and applications of the electromagnetic field emitter 980 and the wearable device 900 to detect and/or alter properties of elements of the environment of the wearable device 900

(e.g., blood, analytes, functionalized nanodiamonds, functionalized magnetic particles) are anticipated.

The wearable device 900 may also include a user interface 990 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 990 may include a display 992 where a visual indication of the alert or recommendation may be displayed. The display 992 may further be configured to provide an indication of the measured physiological parameters, for instance, the concentrations of certain blood analytes being measured.

Figure 10A:
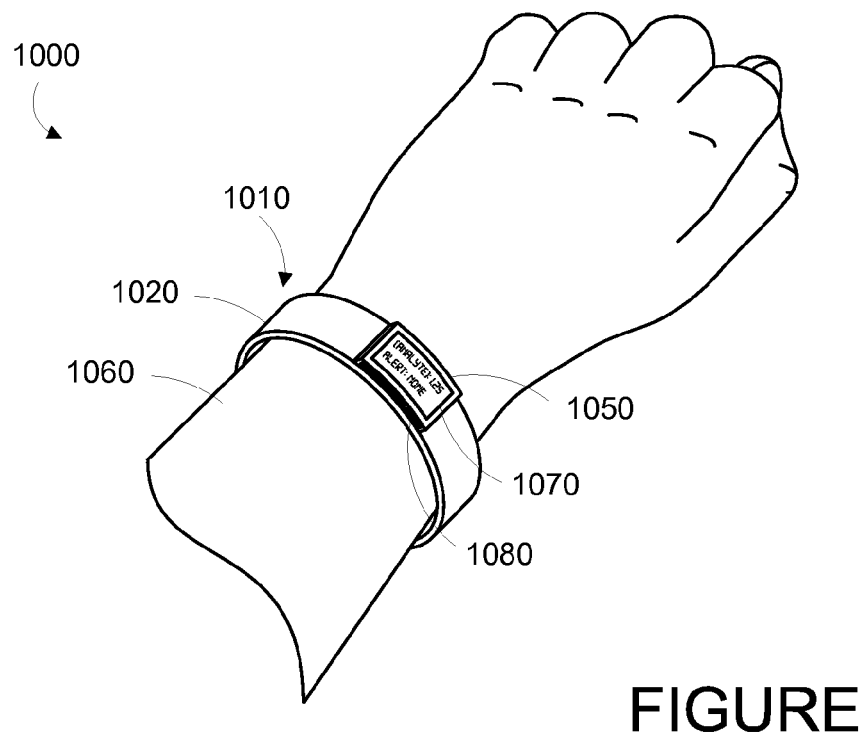
FIG. 10A is a perspective top view of an example wrist-mounted device, when mounted on a wearer's wrist.
Figure 10B:
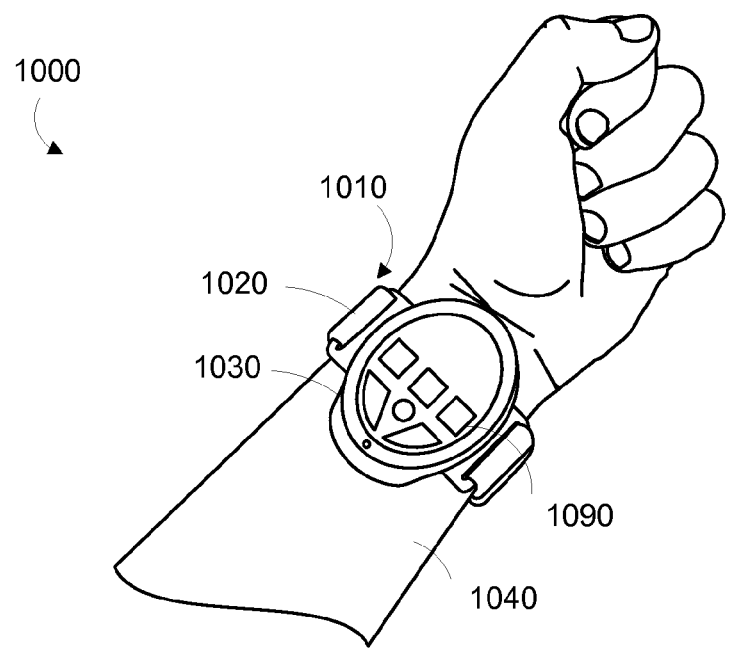
FIG. 10B is a perspective bottom view of an example wrist-mounted device shown in FIG. 10A, when mounted on a wearer's wrist.

In some examples, the wearable device is provided as a wrist-mounted device, as shown in FIGS. 10A, 10B, 11A-11C, 12A, 12B, 13, and 14. The wrist-mounted device may be mounted to the wrist of a living subject with a wristband or cuff, similar to a watch or bracelet. As shown in FIGS. 10A and 10B, the wrist mounted device 1000 may include a mount 1010 in the form of a wristband 1020, a measurement platform 1030 positioned on the anterior side 1040 of the wearer's wrist, and a user interface 1050 positioned on the posterior side 1060 of the wearer's wrist. The wearer of the device may receive, via the user interface 1050, one or more recommendations or alerts generated either from a remote server or other remote computing device, or alerts from the measurement platform. Such a configuration may be perceived as natural for the wearer of the device in that it is common for the posterior side 1060 of the wrist to be observed, such as the act of checking a wrist-watch. Accordingly, the wearer may easily view a display 1070 on the user interface. Further, the measurement platform 1030 may be located on the anterior side 1040 of the wearer's wrist where the subsurface vasculature may be readily observable. However, other configurations are contemplated.

The display 1070 may be configured to display a visual indication of the alert or recommendation and/or an indication of the measured physiological parameters, for instance, the presence or concentrations of certain blood analytes being measured. Further, the user interface 1050 may include one or more buttons 1080 for accepting inputs from the wearer. For example, the buttons 1080 may be configured to change the text or other information visible on the display 1070. As shown in FIG. 10B, measurement platform 1030 may also include one or more buttons 1090 for accepting inputs from the wearer. The buttons 1090 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 11A:
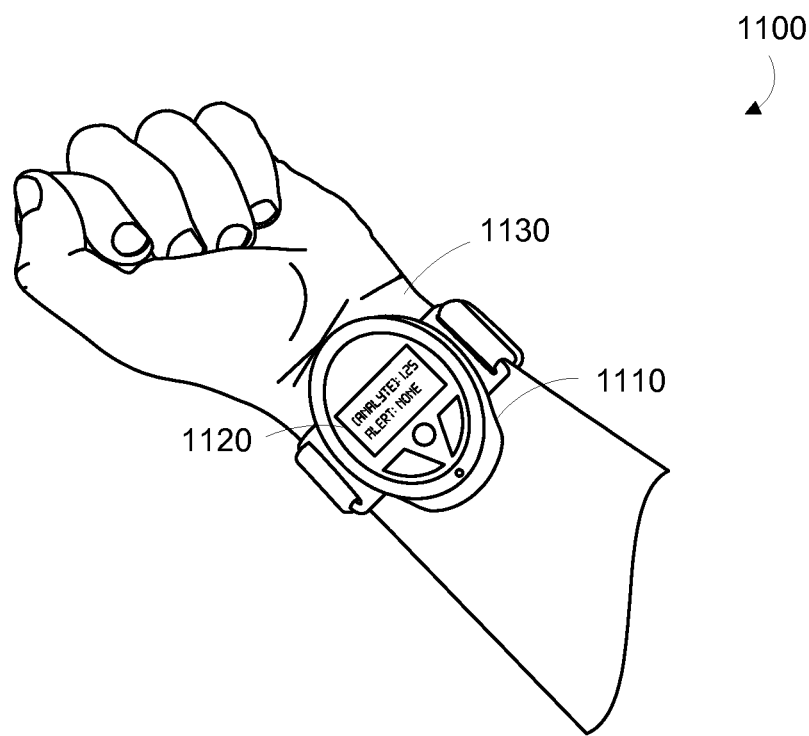
FIG. 11A is a perspective bottom view of an example wrist-mounted device, when mounted on a wearer's wrist.
Figure 11B:
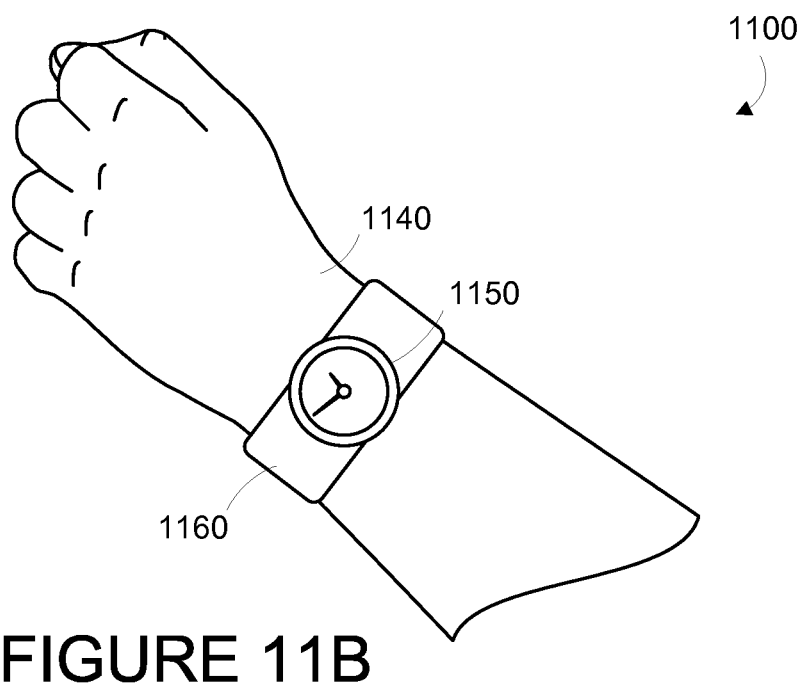
FIG. 11B is a perspective top view of an example wrist-mounted device shown in FIG. 11A, when mounted on a wearer's wrist.
Figure 11C:
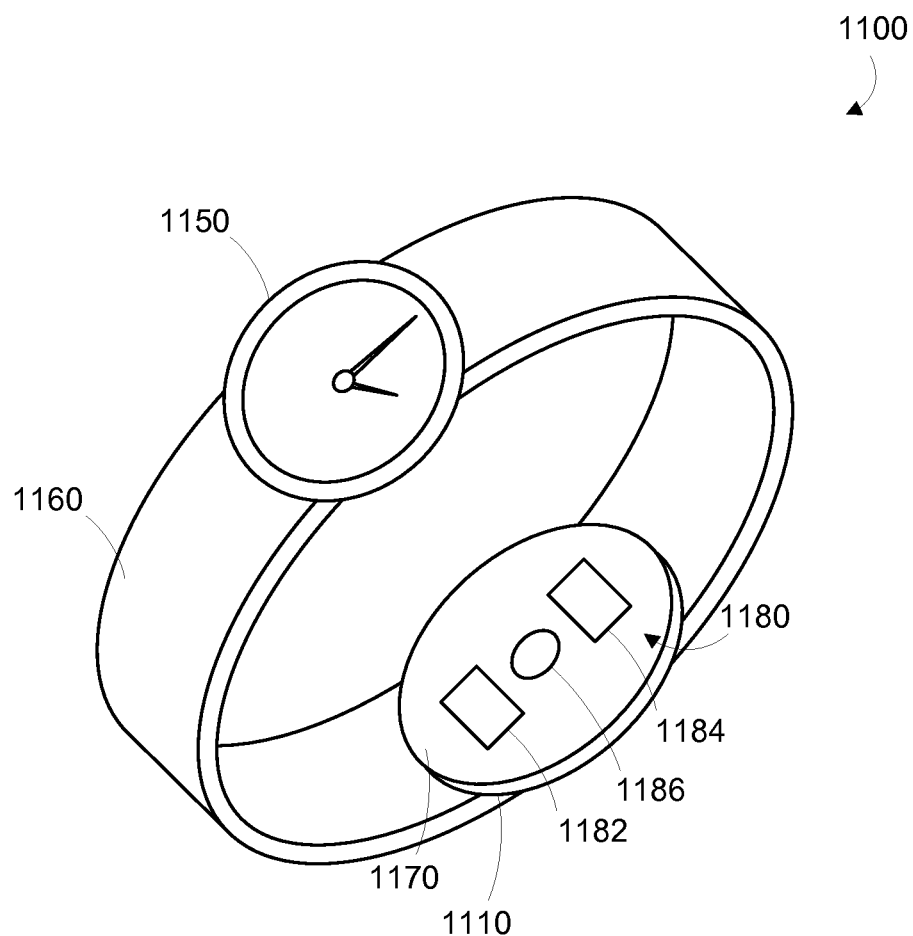
FIG. 11C is a perspective view of an example wrist-mounted device shown in FIGS. 11A and 11B.

In another example wrist-mounted device 1100, shown in FIGS. 11A-11C, the measurement platform 1110 and user interface 1120 are both provided on the same side of the wearer's wrist, in particular, the anterior side 1130 of the wrist. On the posterior side 1140, a watch face 1150 may be disposed on the strap 1160. While an analog watch is depicted in FIG. 11B, one of ordinary skill in the art will recognize that any type of clock may be provided, such as a digital clock.

As can be seen in FIG. 11C, the inner face 1170 of the measurement platform 1110 is intended to be worn proximate to the wearer's body. A data collection system 1180 housed on the measurement platform 1110 may include a detector 1182, a light source 1184, and an electromagnetic field emitter 1186.

Figure 12A:
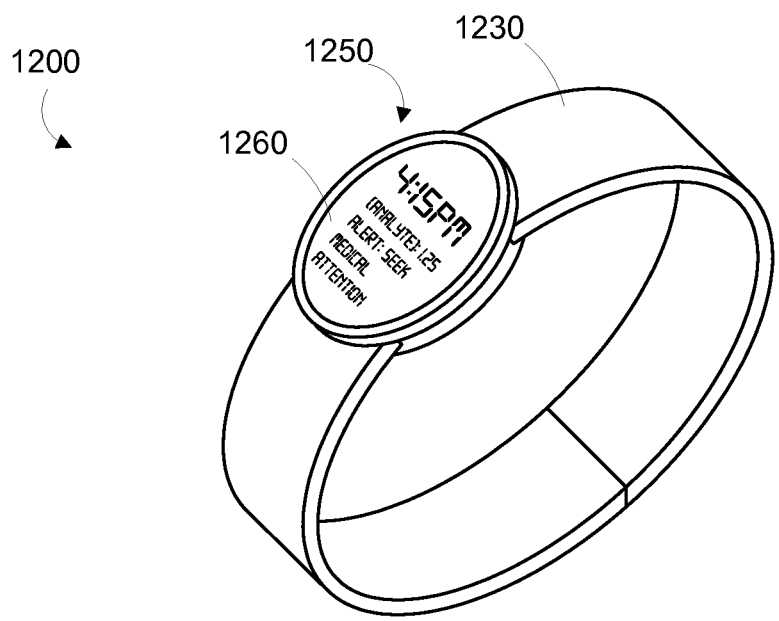
FIG. 12A is a perspective view of an example wrist-mounted device.
Figure 12B:
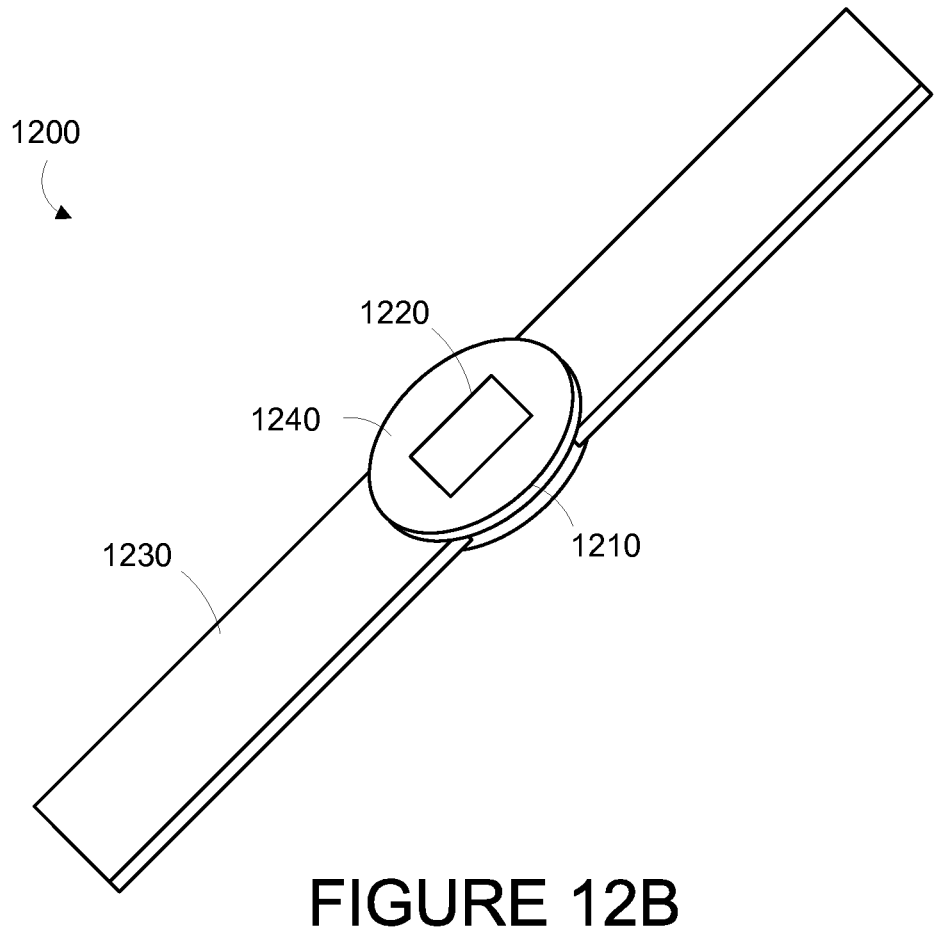
FIG. 12B is a perspective bottom view of an example wrist-mounted device shown in FIG. 12A.

In a further example shown in FIGS. 12A and 12B, a wrist mounted device 1200 includes a measurement platform 1210, which includes a data collection system 1220, disposed on a strap 1230. Inner face 1240 of measurement platform may be positioned proximate to a body surface so that data collection system 1220 may interrogate the subsurface vasculature of the wearer's wrist. A user interface 1250 with a display 1260 may be positioned facing outward from the measurement platform 1210. As described above in connection with other embodiments, user interface 1250 may be configured to display data collected from the data collection system 1220, including the presence and/or concentration of one or more measured analytes, and one or more alerts generated by a remote server or other remote computing device, or a processor located on the measurement platform. The user interface 1220 may also be configured to display the time of day, date, or other information that may be relevant to the wearer.

Figure 13:
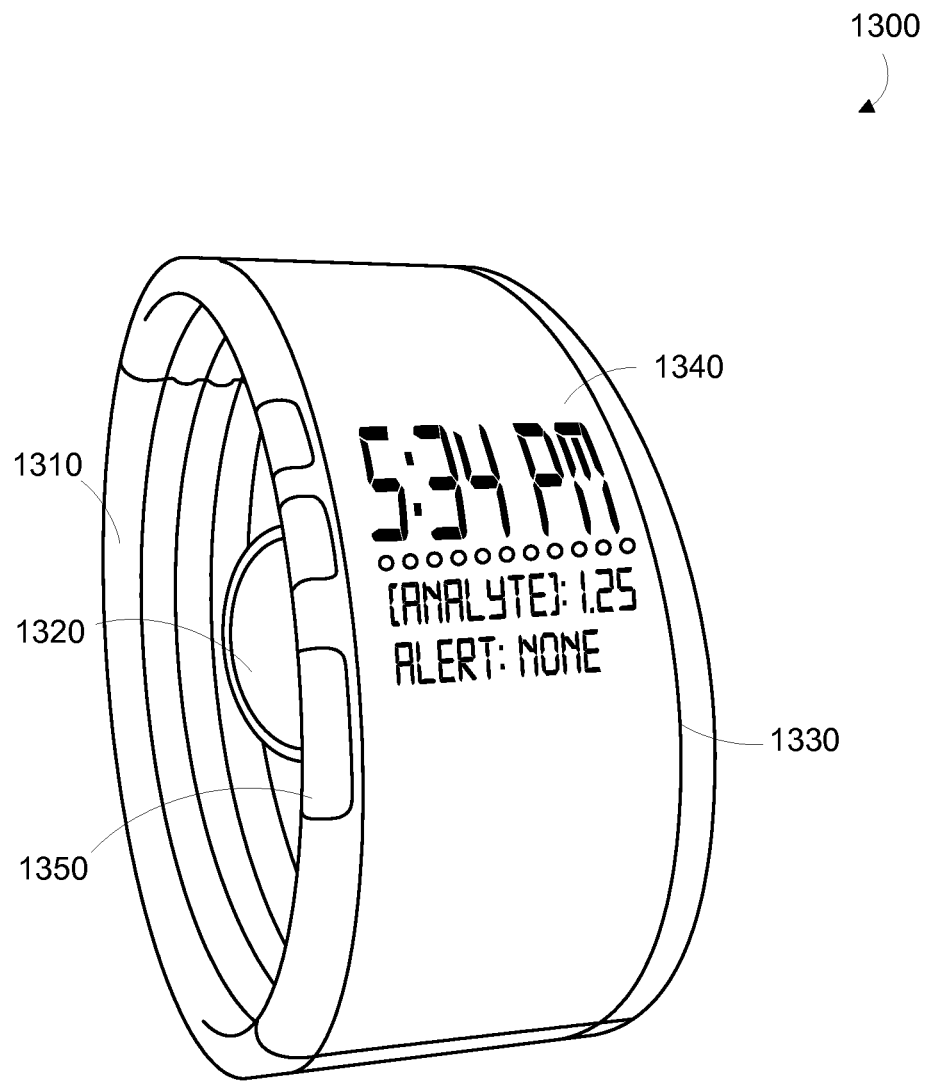
FIG. 13 is a perspective view of an example wrist-mounted device.
Figure 14:
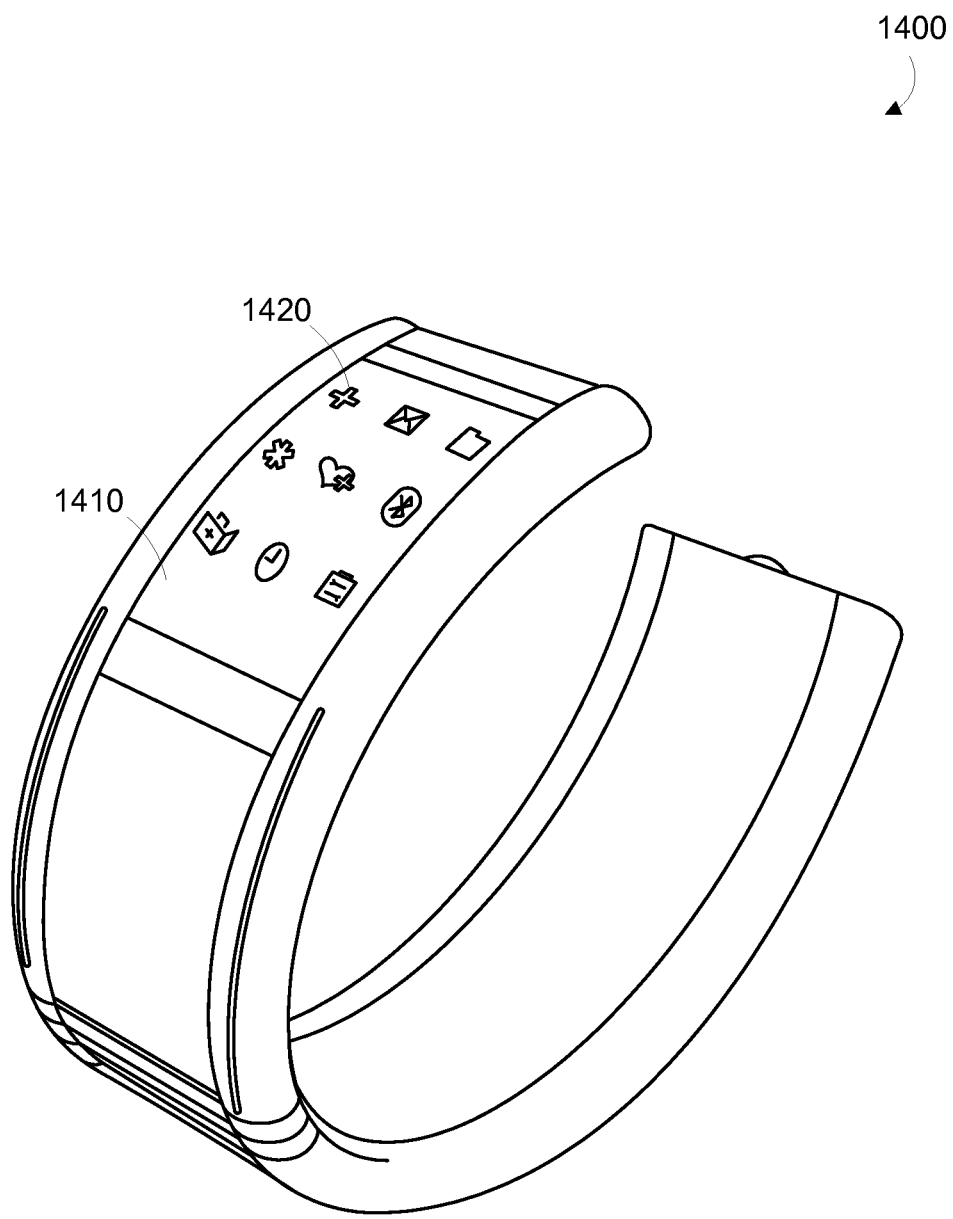
FIG. 14 is a perspective view of an example wrist-mounted device.

As shown in FIG. 13, in a further embodiment, wrist-mounted device 1300 may be provided on a cuff 1310. Similar to the previously discussed embodiments, device 1300 includes a measurement platform 1320 and a user interface 1330, which may include a display 1340 and one or more buttons 1350. The display 1340 may further be a touch-screen display configured to accept one or more input by the wearer. For example, as shown in FIG. 14, display 1410 may be a touch-screen configured to display one or more virtual buttons 1420 for accepting one or more inputs for controlling certain functions or aspects of the device 1400, or inputs of information by the user, such as current health state.

Figure 15:
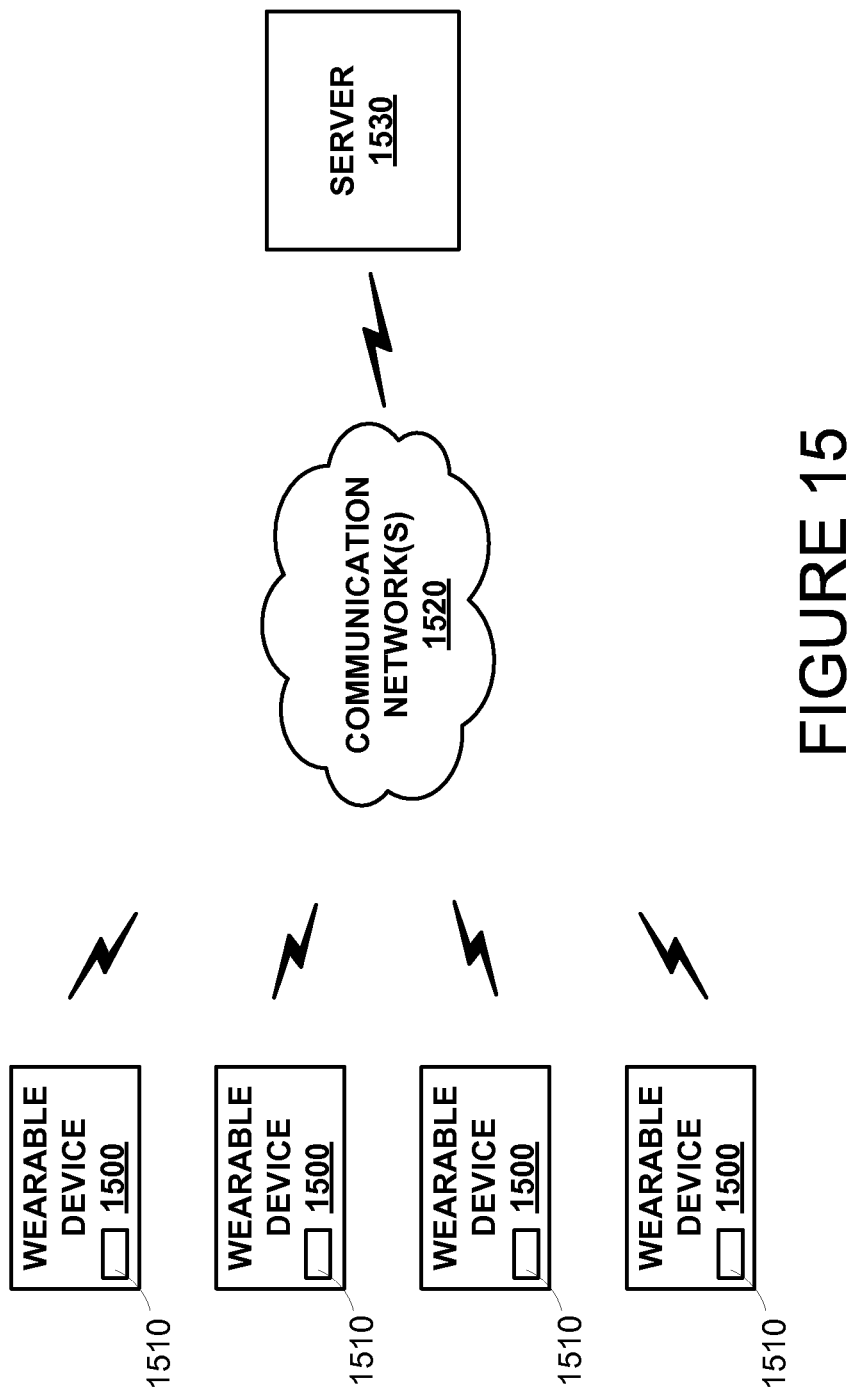
FIG. 15 is a block diagram of an example system that includes a plurality of wearable devices in communication with a server.

FIG. 15 is a simplified schematic of a system including one or more wearable devices 1500. The one or more wearable devices 1500 may be configured to transmit data via a communication interface 1510 over one or more communication networks 1520 to a remote server 1530. In one embodiment, the communication interface 1510 includes a wireless transceiver for sending and receiving communications to and from the server 1530. In further embodiments, the communication interface 1510 may include any means for the transfer of data, including both wired and wireless communications. For example, the communication interface may include a universal serial bus (USB) interface or a secure digital (SD) card interface. Communication networks 1520 may be any one of may be one of: a plain old telephone service (POTS) network, a cellular network, a fiber network and a data network. The server 1530 may include any type of remote computing device or remote cloud computing network. Further, communication network 1520 may include one or more intermediaries, including, for example wherein the wearable device 1500 transmits data to a mobile phone or other personal computing device, which in turn transmits the data to the server 1530.

In addition to receiving communications from the wearable device 1500, such as collected physiological parameter data and data regarding health state as input by the user, the server may also be configured to gather and/or receive either from the wearable device 1500 or from some other source, information regarding a wearer's overall medical history, environmental factors and geographical data. For example, a user account may be established on the server for every wearer that contains the wearer's medical history. Moreover, in some examples, the server 1530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 16:
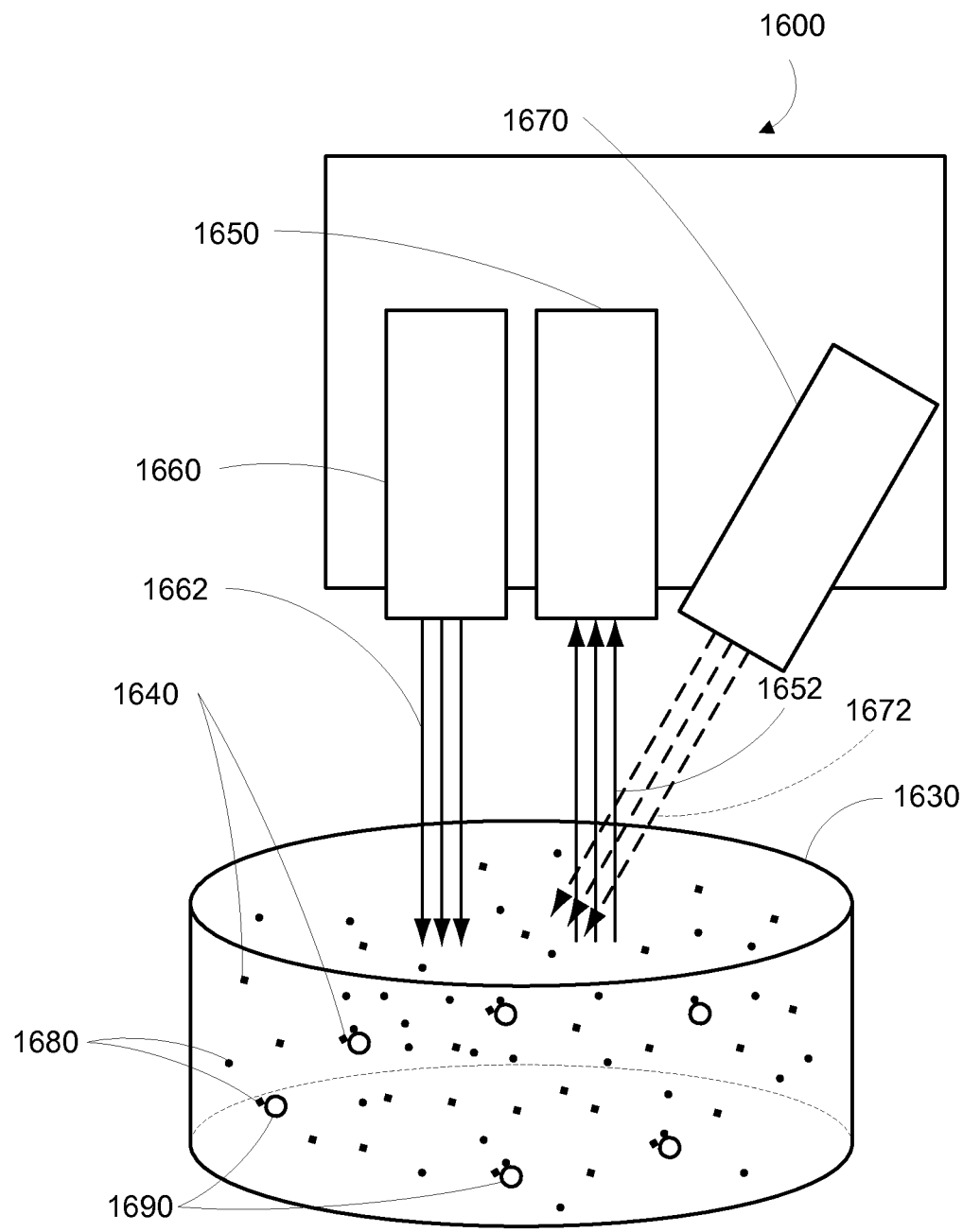
FIG. 16 is a perspective view of an example device.

A device 1600 as illustrated in FIG. 16 can determine one or more properties of an analyte 1690 in an environment 1630 by detecting one or more properties of light emitted by color center-containing functionalized nanodiamonds 1640 in the environment 1630. The biological environment 1630 can be any environment containing analytes of interest 1690 such that functionalized nanodiamonds 1640 and functionalized magnetic particle 1680 in the environment can selectively interact with the analyte of interest 1690 and such that color centers in the functionalized nanodiamonds 1640 can be excited by illumination 1662 from the device 1600 and at least one property of emitted light 1652 emitted by the functionalized nanodiamonds 1630 can be detected by the device 1600. Further, the at least one property of the emitted light 1652 is related to the proximity between the color centers contained in the functionalized nanodiamonds 1640 and the functionalized magnetic particles 1680.

The environment 1630 could be an in vivo biological environment (e.g., a tissue of a living human, animal, plant, etc.) or an in vitro environment. The environment 1630 could be a biological sample in a sample container, cuvette, pipette, microscope slide, or other vessel. The environment 1630 could be part of a biological or chemical process. For example, the biological environment could be a fluid in a water treatment process, a fluid in a food or drug preparation process, a lake, stream, or river in a natural environment, or some other environment. The environment 1630 could be a liquid, a gel, a solid, or some other phase of matter or combination of phases (e.g., an emulsion). The environment 1630 could include biological samples that had been freeze-dried, desiccated, frozen, vaporized, alkalated, or otherwise prepared, including adding the functionalized nanodiamonds 1640 and functionalized magnetic particles 1680 to the environment.

The device 1600 includes a light sensor 1650 configured to detect one or more properties of emitted light 1652 emitted by color centers in functionalized nanodiamonds 1630 in the environment 1630 proximate to the device 1600. The light sensor 1650 could include one or more filters to block light of wavelengths other than the light having wavelengths corresponding to the wavelengths of light emitted by the color centers in response to illumination. For example, the color centers could be negatively-charged nitrogen vacancy centers and the filters could block light having wavelengths other than wavelengths between approximately 600 and 850 nanometers. In some examples, the light sensor 1650 could include a filter that is configured to substantially block light emitted by a light source 1650 of the device 1600.

The device 1600 further includes a light source 1660 for transmitting illumination 1662 that can penetrate the environment 1630 and illuminate the functionalized nanodiamonds 1640. The transmitted illumination 1662 can be any kind of illumination that results at least in emission of light by color centers in the functionalized nanodiamonds 1640 proximate to the device 1600. In some examples, the color centers could be negatively-charged nitrogen vacancy centers and the transmitted illumination 1662 could have a wavelength between approximately 500 nanometers and approximately 650 nanometers. The wavelength of the transmitted illumination 1662 could be specified to penetrate a biological tissue in the environment; for example, the transmitted illumination 1662 could have a wavelength within one or both of the near-infrared (NIR) transparency windows of biological tissue. Exposure to the transmitted illumination 1662 could result in damage and/or irreversible damage to elements of the environment 1662 in examples where the biological environment 1630 is not part of a living human or animal or the environment 1630 does not include samples that cannot be damaged, according to an application.

An electromagnetic field emitter 1670 may also be included in device 1600. In such embodiments, the electromagnetic field emitter 1670 may be configured to emit a variety of electrical, magnetic, and/or electromagnetic fields 1672 into the environment 1630 to enable a variety of methods of detecting and/or determining properties of the environment 1630, functionalized nanodiamonds 1640, functionalized magnetic particles 1680, and/or analytes 1690 proximate to the device 1600. In some examples, the electromagnetic field emitter 1670 could be configured to emit microwave radiation 1672 having a specified frequency. In some examples, the electromagnetic field emitter 1670 could be configured to emit electromagnetic radiation 1672 configured to affect and/or control the occupancy of one or more spin or other quantum states of one or more color centers contained in the functionalized nanodiamonds 1640. In some examples, the electromagnetic field emitter 1670 could be configured to emit an oscillating magnetic field 1672 such that the functionalized magnetic particles 1680 are heated by energy from the oscillating magnetic field 1672. In some examples, the electromagnetic field emitter 1670 could be configured to emit a DC magnetic field. In some examples, the electromagnetic field emitter 1670 could be configured to emit electromagnetic pulses configured to affect and/or control a direction, precession frequency, and/or some other property of a spin or other quantum state of one or more color centers contained in the functionalized nanodiamonds 1640.

The light sensor 1650, electromagnetic field emitter 1670, and light source 1660 could be configured as illustrated in FIG. 16 (i.e., separate, parallel, non-coaxial) or could be configured in another way, according to an application. In some examples, the light sensor 1650 and light source 1660 could be coupled to a set of optical elements to enable some function. For example, the light source 1660 and light sensor 1650 could each include an aperture and could be optically coupled to a beam splitter and other optics to enable the device 1600 to be operated as a confocal microscope. In another example, the light source 1660 could include two light sources configured to produce beams of illumination, where the directions of the beams are controllable using some apparatus, for example a set of galvanometer-driven mirrors. The galvanometers could be operated such that functionalized nanodiamonds 1640 in specified regions (where the beams from the light sources overlap) could be illuminated such that color centers in the functionalized nanodiamonds 1640 in the specified regions emitted light. Other configurations and applications are anticipated.

The device 1600 could be configured to enable other imaging modalities and/or to operate in concert with other devices configured to enable other imaging modalities. In some examples, the device 1600 could include elements to enable magnetic resonance imaging. In some examples, a magnetic field generator could be used to alter properties of color centers in the functionalized nanodiamonds 1640 in the biological environment 1640 to enable other forms of imaging using the functionalized nanodiamonds 1640 and the functionalized magnetic particles 1680 and/or to enable the imaging of the analyte 1690 in specific regions of the environment 1630. Additionally or alternatively, the multiple imaging modalities could be used in a complementary fashion to enable some function. For example, the device 1600 could be used to image the analyte 1690 (e.g., a cancerous growth) in the environment (e.g., a tissue of a human) at the same time magnetic resonance imaging was used to image some other properties of the environment (e.g., soft tissue boundaries) in order to perform some manipulation of the environment 1630 (e.g., a surgical resection of the cancerous growth while minimizing damage to soft tissues surrounding the cancerous growth).

V. Example Electronics Platform for a Device

Figure 17:
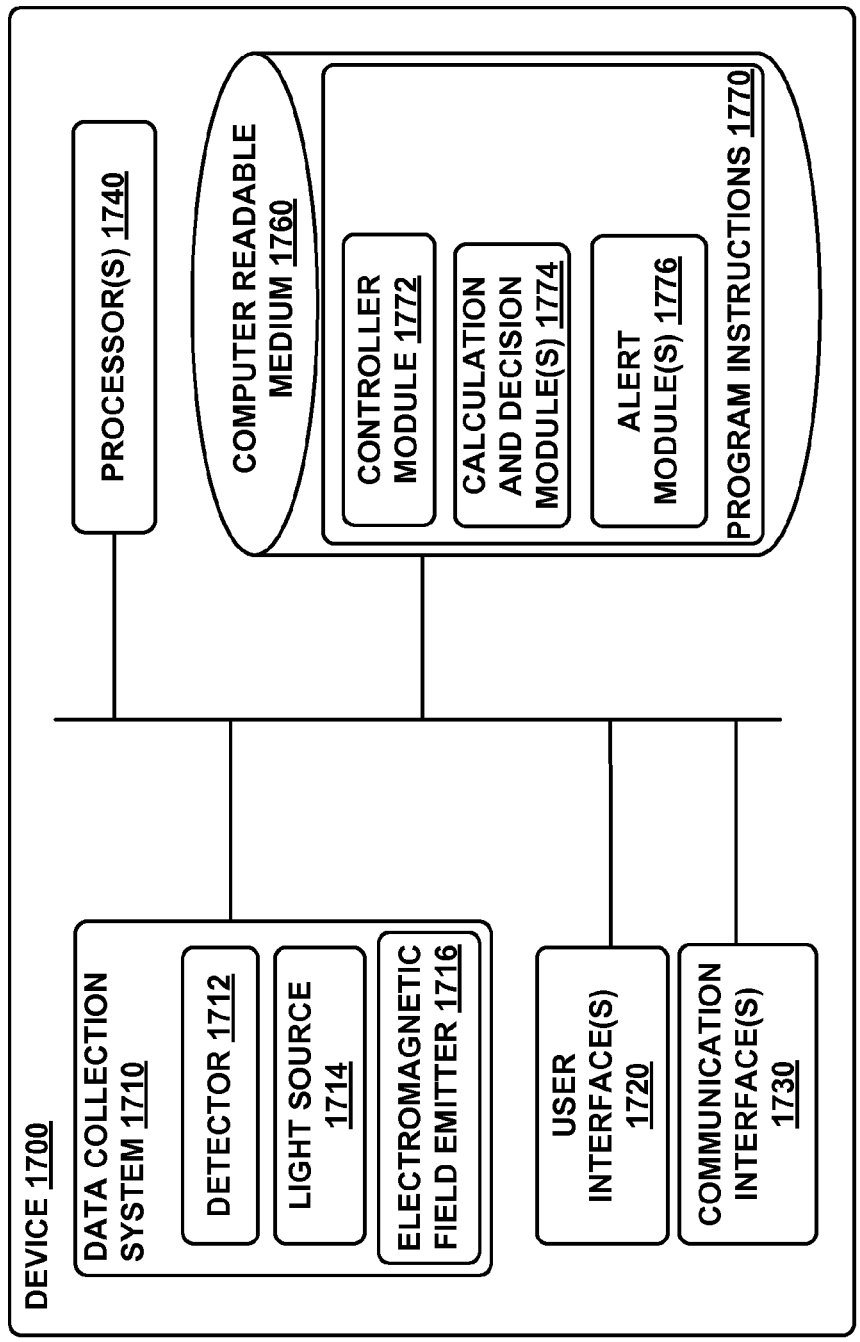
FIG. 17 is a functional block diagram of an example device.

FIG. 17 is a simplified block diagram illustrating the components of a device 1700, according to an example embodiment. Device 1700 may take the form of or be similar to one of the wrist-mounted devices 900, 1000, 1100, 1200, 1300, 1400, shown in FIGS. 9, 10A-B, 11A-11C, 12A-12B, 13 and 14. However, device 1700 may also take other forms, such as an ankle, waist, or chest-mounted device. Device 1700 could also take the form of a device that is not configured to be mounted to a body. For example, device 1700 could take the form of a handheld device configured to be maintained in proximity to an environment of interest (e.g., a body part, a biological sample container, a volume of a water treatment system) by a user or operator of the device 1700 or by a frame or other supporting structure. Device 1700 could also take the form of a device configured to illuminate and to detect emitted light from an in vitro biological environment or some other environment, for example, a fluid volume within a water treatment process. Device 1700 also could take other forms (e.g., device 1600 illustrated in FIG. 16).

In particular, FIG. 17 shows an example of a wearable device 1700 having a data collection system 1710, a user interface 1720, communication interface 1730 for transmitting data to a remote system, and processor(s) 1740. The components of the wearable device 1700 may be disposed on a mount or on some other structure for mounting the device to enable stable detection of one or more properties of functionalized nanodiamonds, functionalized magnetic particles, and analytes particles in an environment of interest, for example, to an external body surface where a portion of subsurface vasculature is readily observable.

Processor 1740 may be a general-purpose processor or a special purpose processor (e.g., digital signal processors, application specific integrated circuits, etc.). The one or more processors 1740 can be configured to execute computer-readable program instructions 1770 that are stored in the computer readable medium 1760 and that are executable to provide the functionality of a device 1700 described herein.

The computer readable medium 1760 may include or take the form of one or more non-transitory, computer-readable storage media that can be read or accessed by at least one processor 1740. The one or more computer-readable storage media can include volatile and/or non-volatile storage components, such as optical, magnetic, organic or other memory or disc storage, which can be integrated in whole or in part with at least one of the one or more processors 1740. In some embodiments, the computer readable medium 1760 can be implemented using a single physical device (e.g., one optical, magnetic, organic or other memory or disc storage unit), while in other embodiments, the computer readable medium 1760 can be implemented using two or more physical devices.

Data collection system 1710 includes detectors 1712, a light source 1714, and an electromagnetic field emitter 1716. As described above, detectors 1712 may include any detector capable of detecting at least one property, which could include any properties that may relate to the environment being analyzed by the device. For example, the detectors 1712 could be configured to measure blood pressure, pulse rate, skin temperature, etc. In some examples, detectors 1712 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

At least one of the detectors 1712 is a light sensor configured to detect one or more properties of light emitted by color centers in functionalized nanodiamonds in the environment proximate to the wearable device 1700. The light sensor could be a photodiode, a photomultiplier, a CCD, a photocell, a photoresistive element, a camera, or any other sensor or sensors configured to detect one or more properties of light emitted by color centers of the functionalized nanodiamonds.

The color centers of the functionalized nanodiamonds emit light in response to illumination of the color centers, and the detected one or more properties of the emitted light are related to the proximity between the color centers and functionalized magnetic particles in the environment. The light sensor could include a filter that is configured to substantially block light emitted by the light source 1714 of the data collection system 1710.

The data collection system 1710 further includes a light source 1714 for transmitting illumination that can penetrate the environment to illuminate the color centers contained in the functionalized nanodiamonds. The wavelength of the transmitted illumination could be specified to penetrate biological tissues of a wearer; for example, the transmitted illumination could have a wavelength within a near-infrared (NIR) transparency window of biological tissue. The wavelength of the transmitted illumination could be specified to be a wavelength that causes fluorescence and/or emission of light by the color centers. In some examples, the color centers could be negatively-charged nitrogen vacancy centers, and the wavelength of the transmitted illumination could be between approximately 500 and 650 nanometers. The light source 1714 could be configured to produce additional illumination that results in emission of light by other chemicals, imaging agents, biological elements, or other analytes proximate to the light source 1714.

An electromagnetic field emitter 1716 may also be included in the data collection system 1710. In such embodiments, the electromagnetic field emitter 1716 may be configured to emit a variety of electrical, magnetic, and/or electromagnetic fields into the environment to enable a variety of methods of detecting and/or determining properties of the environment, functionalized nanodiamonds, functionalized magnetic particles, and/or analytes proximate to the device 1700. In some examples, the electromagnetic field emitter 1716 could be configured to emit microwave radiation having a specified frequency. In some examples, the electromagnetic field emitter 1716 could be configured to emit electromagnetic radiation configured to affect and/or control the occupancy of one or more spin or other quantum states of one or more color centers contained in the functionalized nanodiamonds. In some examples, the electromagnetic field emitter 1716 could be configured to emit an oscillating magnetic field such that the functionalized magnetic particles are heated by energy from the oscillating magnetic field. In some examples, the electromagnetic field emitter 1716 could be configured to emit a DC magnetic field. In some examples, the electromagnetic field emitter 1716 could be configured to emit electromagnetic pulses configured to affect and/or control a direction, precession frequency, and/or some other property of a spin or other quantum state of one or more color centers contained in the functionalized nanodiamonds.

The electromagnetic field emitter 1716 could employ more than one of the methods disclosed herein or elsewhere to control, induce, modulate, or otherwise affect one or more properties of functionalized nanodiamonds, functionalized magnetic particles, analytes, or other element in an environment of interest. In some examples, acoustic waves could be emitted into the environment to selectively heat functionalized acoustic absorbers; the temperature of functionalized nanodiamonds in the environment could be detected and used to determine a proximity between the functionalized nanodiamonds and the functionalized acoustic absorbers. In some examples, the electromagnetic field emitter 1716 could generate continuous and/or pulsed microwave energy to manipulate a direction of spins of color centers in functionalized nanodiamonds in the environment. For example, the continuous and/or pulsed microwave energy could be used to manipulate spins of color centers according to techniques used in nuclear magnetic resonance spectroscopy, nuclear magnetic resonance imaging, or other magnetic resonance techniques. Other operations and applications of the electromagnetic field emitter 1716 and the device 1700 to detect and/or alter properties of elements of the environment of the wearable device 1700 (e.g., blood, analytes, functionalized nanodiamonds, functionalized magnetic particles) are anticipated.

The program instructions 1770 stored on the computer readable medium 1760 may include instructions to perform any of the methods described herein. For instance, in the illustrated embodiment, program instructions 1770 include a controller module 1772, calculation and decision module 1774 and an alert module 1776.

The controller module 1772 can include instructions for operating the data collection system 1710, for example, the detectors 1712, light source 1714, and electromagnetic field emitter 1716. For example, the controller 1772 may operate light source 1714, electromagnetic field emitter 1716, and/or detectors 1712 during each of a set of pre-set measurement periods. In particular, the controller module 1772 can include instructions for operating the light source 1714 to emit illumination into a tissue of a wearer of the device 1700 and controlling the detectors 1712 to detect one or more properties of light emitted by color centers contained in functionalized nanodiamonds in the environment being interrogated by the device 1700.

The controller module 1772 can also include instructions for operating a user interface 1720. For example, controller module 1772 may include instructions for displaying data collected by the data collection system 1710 and analyzed by the calculation and decision module 1774, or for displaying one or more alerts generated by the alert module 1776. Further, controller module 1772 may include instructions to execute certain functions based on inputs accepted by the user interface 1720, such as inputs accepted by one or more buttons disposed on the user interface.

Communication platform 1730 may also be operated by instructions within the controller module 1772, such as instructions for sending and/or receiving information via a wireless antenna, which may be disposed on or in the device 1700. The communication interface 1730 can optionally include one or more oscillators, mixers, frequency injectors, etc. to modulate and/or demodulate information on a carrier frequency to be transmitted and/or received by the antenna. In some examples, the device 1700 is configured to indicate an output from the processor by modulating an impedance of the antenna in a manner that is perceivable by a remote server or other remote computing device.

Calculation and decision module 1772 may include instructions for receiving data from the data collection system 1710, analyzing the data to determine if a target analyte is present or absent, quantify the measured physiological parameter(s), such as concentration of a target analyte, analyzing the data to determine if a medical condition is indicated, or other analytical processes relating to the environment proximate to the device 1700. In particular, the calculation and decision module 1772 may include instructions for determining, for each preset measurement time, the presence, concentration, and/or other properties of a clinically-relevant analyte based on the one or more properties of light emitted by color centers contained in functionalized nanodiamonds in a lumen of subsurface vasculature of a user of the device 1700; and determining whether a medical condition is indicated based on at least the corresponding presence, concentration, or other property of the clinically-relevant analyte. These instructions could be executed at each of a set of preset measurement times.

The program instructions of the calculation and decision module 1772 may, in some examples, be stored in a computer-readable medium and executed by a processor located external to the device 1700. For example, the device 1700 could be configured to collect certain data regarding physiological parameters from the user and then transmit the data to a remote server, which may include a mobile device, a personal computer, the cloud, or any other remote system, for further processing.

The computer readable medium 1760 may further contain other data or information, such as medical and health history of a user of the device 1700, that may be useful in determining whether a medical condition is indicated. Further, the computer readable medium 1760 may contain data corresponding to certain analyte baselines, above or below which a medical condition is indicated. The baselines may be pre-stored on the computer readable medium 1760, may be transmitted from a remote source, such as a remote server, or may be generated by the calculation and decision module 1774 itself. The calculation and decision module 1774 may include instructions for generating individual baselines for the user of the device 1700 based on data collected over a certain number of measurement periods. For example, the calculation and decision module 1774 may generate a baseline concentration of a target blood analyte for each of a plurality of measurement periods by averaging the analyte concentration at each of the measurement periods measured over the course of a few days, and store those baseline concentrations in the computer readable medium 1760 for later comparison. Baselines may also be generated by a remote server and transmitted to the device 1700 via communication interface 1730. The calculation and decision module 1774 may also, upon determining that a medical condition is indicated, generate one or more recommendations for the user of the device 1700 based, at least in part, on consultation of a clinical protocol. Such recommendations may alternatively be generated by the remote server and transmitted to the device 1700.

In some examples, the collected physiological parameter data, baseline profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 1774 that a medical condition is indicated, the alert module 1776 may generate an alert via the user interface 1720. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while imaging agents, devices, systems, methods, and other embodiments are described herein by way of example as being employed to detect properties of one or more analytes in biological environments of a human body, it is noted that the disclosed imaging agents, devices, systems, and methods can be applied in other contexts as well. For example, detection systems configured to detect one or more properties of an analyte using an imaging agent as disclosed herein may be included in wearable (e.g., body-mountable) and/or implantable devices. In some contexts, such a detection system is situated to be substantially encapsulated by bio-compatible polymeric material suitable for being in contact with bodily fluids and/or for being implanted. In one example, a mouth-mountable detection is configured to be mounted within an oral environment, such as adjacent a tooth or adhered to an inner mouth surface. In another example, an implantable medical device that includes such a detection system may be encapsulated in biocompatible material and implanted within a host organism. Such body-mounted and/or implanted detection systems can include circuitry configured to operate light emitters, light sensors, microwave emitters, magnetic field emitters, or other elements to enable detection of properties of an analyte by detecting one or more properties of an imaging agent related to the properties of the analyte. The detection system can also include an energy harvesting system and a communication system for wirelessly indicating detected and/or determined properties of an analyte.

In other examples, imaging agents, devices, systems, and methods disclosed herein may be applied to measure properties of one or more analytes in environments that are not in or on a human body. For example, detection systems disclosed herein may be included in body-mountable and/or implantable devices used to measure analyte properties in a fluid of an animal, where the fluid of the animal additionally includes an imaging agent as described herein. In another example, e imaging agents, devices, systems, and methods disclosed herein may be applied to measure properties of an analyte in an environmental fluid, such as a fluid in a river, lake, marsh, reservoir, water supply, sanitary sewer system, or storm sewer system. In another example, imaging agents, devices, systems, and methods disclosed herein may be applied to measure properties of an analyte in a fluid that is part of a process, such as a waste treatment process, pharmaceutical synthesis process, food preparation process, fermentation process, or medical treatment process Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. An in vivo imaging agent, comprising:
   a plurality of functionalized magnetic nanoparticles, wherein each of the functionalized magnetic nanoparticles is functionalized to selectively interact with an analyte in an environment; and
   a plurality of functionalized nanodiamonds, wherein each of the functionalized nanodiamonds contains at least one color center and is functionalized to selectively interact with the analyte in the environment, and wherein the at least one color center is configured to emit light in response to illumination, wherein the emitted light has one or more properties relating to proximity between the at least one color center and individual functionalized magnetic nanoparticles of the plurality of functionalized magnetic nanoparticles.

2. The in vivo imaging agent of claim 1, wherein the color centers comprise negatively-charged nitrogen vacancy centers.

3. The in vivo imaging agent of claim 1, wherein the plurality of functionalized magnetic nanoparticles comprises magnetic nanoparticles comprising superparamagnetic iron oxide.

4. The in vivo imaging agent of claim 1, wherein each of the functionalized magnetic nanoparticles comprises a ferromagnetic material, a paramagnetic material, or a superparamagnetic material.

5. The in vivo imaging agent of claim 1, wherein each of the functionalized magnetic nanoparticles is functionalized with a receptor, protein, antibody, or nucleic acid sequence.

6. The in vivo imaging agent of claim 1, wherein each of the functionalized nanodiamonds is functionalized with a receptor, protein, antibody, or nucleic acid sequence.

7. The in vivo imaging agent of claim 1, wherein the functionalized magnetic nanoparticles and the functionalized nanodiamonds are functionalized to selectively bind to cancer cells.

8. The in vivo imaging agent of claim 1, wherein the environment is a human body and the analyte is a cancer cell.

9. The in vivo imaging agent of claim 1, wherein the emitted light has one or more properties relating to a magnetic field produced or affected by one or more proximate functionalized magnetic nanoparticles.

10. The in vivo imaging agent of claim 1, wherein the at least one color center exhibits optical properties that are related to a magnetic field in an environment of the at least one color center.

11. The in vivo imaging agent of claim 10, wherein the at least one color center has a plurality of spin states, and wherein occupancy of the spin states is affected by the magnetic field in the environment of the at least one color center.

12. The in vivo imaging agent of claim 11, wherein the occupancy of the spin states affects the one or more properties of the emitted light.

13. The in vivo imaging agent of claim 1, further comprising a fluorophore attached to each of the functionalized magnetic nanoparticles.

14. The in vivo imaging agent of claim 1, further comprising a fluorophore attached to each of the functionalized nanodiamonds.

15. The in vivo imaging agent of claim 1, wherein each of the functionalized magnetic nanoparticles is functionalized by covalent attachment of a bioreceptor, wherein the bioreceptor specifically binds with at least a portion of the analyte.

16. The in vivo imaging agent of claim 1, wherein each of the functionalized nanodiamonds is functionalized by covalent attachment of a bioreceptor, wherein the bioreceptor specifically binds with at least a portion of the analyte.

17. The in vivo imaging agent of claim 1, wherein the color centers are silicon vacancy centers.

18. The in vivo imaging agent of claim 1, wherein each instance of the analyte has at least a first binding site and a second binding site, wherein each of the functionalized magnetic nanoparticles is functionalized to bind with the first binding site, and wherein each of the functionalized nanodiamonds is functionalized to bind with the second binding site.

19. The in vivo imaging agent of claim 18, wherein binding of an instance of the analyte to both a functionalized magnetic nanoparticle via the first binding site and a functionalized nanodiamond via the second binding site is detectable by the one or more properties of the emitted light from the at least one color center of the functionalized nanodiamond based on proximity of the functionalized magnetic nanoparticle and the functionalized nanodiamond.

20. The in vivo imaging agent of claim 1, wherein the one or more properties of the emitted light include amplitude, wavelength, degree of polarization, orientation of polarization, or location of the emitted light.

* * * * *